United States Patent
Wang et al.

(10) Patent No.: US 9,856,483 B2
(45) Date of Patent: Jan. 2, 2018

(54) EXPRESSION SYSTEM FOR PRODUCING PROTEIN HAVING A N-TERMINAL PYROGLUTAMATE RESIDUE

(71) Applicant: Academia Sinica, Taipei (TW)

(72) Inventors: Andrew H. -J. Wang, Taipei (TW); Kai-Fa Huang, Taipei (TW); Yan-Ping Shih, Taipei (TW)

(*) Notice: Subject to any disclaimer, the term of this patent is extended or adjusted under 35 U.S.C. 154(b) by 279 days.

(21) Appl. No.: 14/661,052

(22) Filed: Mar. 18, 2015

(65) Prior Publication Data

US 2016/0273015 A1 Sep. 22, 2016

(51) Int. Cl.
*C12N 15/70* (2006.01)
*C07K 14/52* (2006.01)
*C12P 21/02* (2006.01)
*C12N 9/10* (2006.01)

(52) U.S. Cl.
CPC .............. *C12N 15/70* (2013.01); *C07K 14/52* (2013.01); *C12N 9/104* (2013.01); *C12P 21/02* (2013.01); *C12Y 203/02005* (2013.01); *C07K 2319/21* (2013.01); *C07K 2319/24* (2013.01); *C07K 2319/50* (2013.01)

(58) Field of Classification Search
CPC .................................................... C12N 15/70
See application file for complete search history.

(56) References Cited

PUBLICATIONS

Shih et al., "Linked Production of Pyroglutamate-Modified Proteins via Self-Cleavage of Fusion Tags with TEV Protease and Autonomous N-Terminal Cyclization with Glutaminyl Cyclase In Vivo", PLOS One, Apr. 2014, 9(4):e94812.*
Chelius et al., "Formation of Pyroglutamic Acid from N-Terminal Glutamic Acid in Immunoglobulin Gamma Antibodies", Anal. Chem. 2006, 78, 2370-2376.*
Pan et al., "Structural Characterization of Human Interferon-gamma: Heterogeneity of the carboxyl terminus", Eur. J. Biochem., 1987, 166:145-149.*

* cited by examiner

*Primary Examiner* — Suzanne M Noakes

(57) ABSTRACT

Disclosed herein is an expression system and uses thereof. The expression system comprises two vectors that express two fusion proteins and a glutaminyl cyclase (QC) with E45Q mutation, so as to autonomously produce a target protein having a N-terminal pyroglutamate (pGlu) residue in a host cell. The first fusion protein is composed of a maltose binding protein (MBP) and a tobacco etch virus protease (TEVP); and the second fusion protein includes in sequence, a thioredoxin, a S-tag, a linker having a TEVP recognition site therein, a target protein, and a $(His)_{6}$-tag. The second fusion protein is cleaved by the TEVP that is expressed by the first fusion protein, and then catalyzed by QC with E45Q mutation so as to autonomously produce the target protein having a N-terminal pGlu residue in the host cell.

20 Claims, 9 Drawing Sheets

U.S. 9,856,483 B2

EXPRESSION SYSTEM FOR PRODUCING PROTEIN HAVING A N-TERMINAL PYROGLUTAMATE RESIDUE

SEQUENCE LISTING

The present invention disclosure includes a sequence listing incorporated herein by reference in its entirety.

BACKGROUND OF THE INVENTION

Field of the Invention

The present disclosure in general relates to an expression system. More particularly, the present disclosure relates to an expression system for the production of a protein that has a N-terminal pyroglutamate (pGlu) residue.

Description of Related Art

Cyclization of a glutaminyl or glutamyl residue to form a pyroglutamate (5-oxoproline, pGlu) residue occurs at the N-terminus of numerous secretory proteins and peptides. The N-terminal pGlu modification is known to protect the proteins and peptides from exopeptidase degradation, and endow them with a proper conformation for binding to their receptors. To date, a large number of proteins and peptides with N-terminal pGlu modification have been reported, including thyrotropin-releasing hormone (TRH), gonadotropin-releasing hormone (GnRH), neurotensin, gastrin, glucagon, monocyte chemoattractant protein (MCP), immunoglobulin, and ribonuclease.

The N-terminal pGlu formation on proteins and peptides are catalyzed by glutaminyl cyclase (QC). Two types of QCs have been reported. Type I QCs display a five-bladed β-propeller fold and are mainly identified in plants, pathogenic bacteria, and human parasites; and type II QCs adopt an α/β topology and are abundant in the neuroendocrine tissues and peripheral blood lymphocytes of mammals. Within the mammalian cells, QCs are mainly identified in the secretory granules and Golgi apparatus, where majorities of secreted hormones and chemokines are present.

Tobacco etch virus protease (TEVP), a cysteine protease, recognizes and exhibits high cleavage efficacy toward the sequence EXLYφQ\φ, in which X is any residue, φ is any large or medium hydrophobic residue, and φ is any small hydrophobic residue. Based on the cleavage specificity, TEVP is usually used as a biological tool to remove the tag protein that is linked with a target protein by the TEVP recognition sequence. However, TEVP is insoluble in water; thus, a carrier protein that exhibits the ability to prevent protein aggregation, such as the maltose-binding protein (MBP) and the N-utilizing substance A (NusA), is generally needed to be co-expressed with TEVP so as to increase its solubility.

Generation of N-terminal pGlu-modified proteins by either *Escherichia coli* (*E. coli*) or eukaryotic cells is a challenging work, due to the fact that the fusion protein cannot be recovered without the following two-step reaction: (1) the removal of tag protein by protease to expose the N-terminal glutaminyl or glutamyl residue, and (2) converting the exposed glutaminyl or glutamyl residue into a pGlu residue, a cyclization reaction catalyzed by QC. The two-step reaction not only limits the production efficiency, but also substantially reduces the product yield.

In view of the forgoing, there exists in the related art a need for an improved expression system and/or method that produce N-terminal pGlu-modified proteins without performing the conventional two-step reaction.

SUMMARY

The following presents a simplified summary of the disclosure in order to provide a basic understanding to the reader. This summary is not an extensive overview of the disclosure and it does not identify key/critical elements of the present invention or delineate the scope of the present invention. Its sole purpose is to present some concepts disclosed herein in a simplified form as a prelude to the more detailed description that is presented later.

As embodied and broadly described herein, one aspect of the present disclosure pertains to an expression system for producing a target protein having a N-terminal pGlu residue in a host cell. The expression system comprises:

(a) a first vector comprising a first nucleotide sequence that encodes a first fusion protein, from the N-terminus to C-terminus, a maltose binding protein (MBP) and a tobacco etch virus protease (TEVP); and (b) a second vector comprising in sequence, (b-1) a second nucleotide sequence that encodes a second fusion protein, from the N-terminus to C-terminus, a thioredoxin (Trx), a S-tag, a linker having a TEVP recognition site (rsTEV) therein, the target protein, and a (His)$_6$-tag; and (b-2) a third nucleotide sequence that encodes a glutaminyl cyclase (QC) having a E45Q mutation;

wherein, the second nucleotide sequence is characterized in having two restriction endonuclease cleavage sites respectively located within the linker, and between the target protein and the (His)$_6$-tag; and the N-terminal pGlu residue of the target protein is autonomously formed in the host cell.

According to one embodiment of the present disclosure, the two restriction endonuclease cleavage sites in the second nucleotide sequence are respectively SnaB I, which is located within the linker, and Xho I, which is located between the target protein and the (His)$_6$-tag.

According to another embodiment of the present disclosure, the first nucleotide sequence is at least 90% identical to SEQ ID NO: 1, and the first fusion protein encoded thereof has an amino acid sequence at least 90% identical to SEQ ID NO: 5; the second nucleotide sequence is at least 90% identical to SEQ ID NO: 2 or 3, and the second fusion protein encoded thereof has an amino acid sequence at least 90% identical to SEQ ID NO: 6 or 7; the third nucleotide sequence is at least 90% identical to SEQ ID NO: 4, and the QC with a E45Q mutation (i.e., QC(E45Q)) encoded thereof has an amino acid sequence at least 90% identical to SEQ ID NO: 8.

In some embodiments of the present disclosure, the first, second, and third nucleotide sequences are respectively driven by a first, a second, and a third promoters, in which each of the first, second, and third promoter is selected from the group consisting of T5, T7, tac, trc, lac, lacUV5, araBAD, and rhaBAD. According to one specific embodiment, all the first, second, and third promoters are T7 promoters.

According to the embodiment of the present disclosure, the target protein is any of a hormone, a cytokine, a chemokine, an immunoglobulin, or a ribonuclease. Specifically, the chemokine is monocyte chemoattractant protein 1 (MCP1) or MCP2; the hormone is any of thyrotropin-releasing hormone, gonadotropin-releasing hormone, neurotensin, gastrin, or glucagon; the cytokine is antineoplastic urinary protein (ANUP) or interferon-γ (IFN-γ); and the immunoglobulin is an antibody with a glutaminyl residue or a glutamyl residue on the N-terminus of light chain or heavy chain. According to the embodiment of the present disclosure, the ribonuclease is a frog ribonuclease, in which the frog is selected from the group consisting of *Rana pepeins, Rana japonica*, and *Rana catesbeana*.

In one working example of the present disclosure, the host cell is an *Escherichia coli* (*E. coli*) cell.

Another aspect of the present disclosure is directed to a method of producing a target protein having a N-terminal pGlu residue in a host cell. The method comprises:

(a) transducing the host cell with the present expression system;

(b) cultivating the transduced host cell of step (a) in a culture medium;

(c) lysing the cultivated host cell of step (b); and (d) purifying the target protein from the supernatant of the lysed product of step (c) by affinity chromatography.

According to the embodiments of the present disclosure, the target protein can be any of a hormone, a cytokine, a chemokine, an immunoglobulin, or a ribonuclease. In one specific embodiment, the chemokine is MCP1 or MCP2; the hormone is any of thyrotropin-releasing hormone, gonadotropin-releasing hormone, neurotensin, gastrin, or glucagon; the cytokine is ANUP or IFN-γ; and the immunoglobulin is an antibody with a glutaminyl residue or a glutamyl residue on the N-terminus of light chain or heavy chain. In another embodiment of the present disclosure, the ribonuclease is a frog ribonuclease, wherein the frog is selected from the group consisting of *Rana pepeins, Rana japonica*, and *Rana catesbeana*.

According to some embodiments of the present disclosure, the host cell used to produce the target protein is an *E. coli* cell.

In the embodiment of the present disclosure, the affinity chromatography employed to purify the target protein is an immobilized metal ion affinity chromatography (MIAC).

Many of the attendant features and advantages of the present disclosure will becomes better understood with reference to the following detailed description considered in connection with the accompanying drawings.

BRIEF DESCRIPTION OF THE DRAWINGS

The present description will be better understood from the following detailed description read in light of the accompanying drawings, where.

Figure 1:
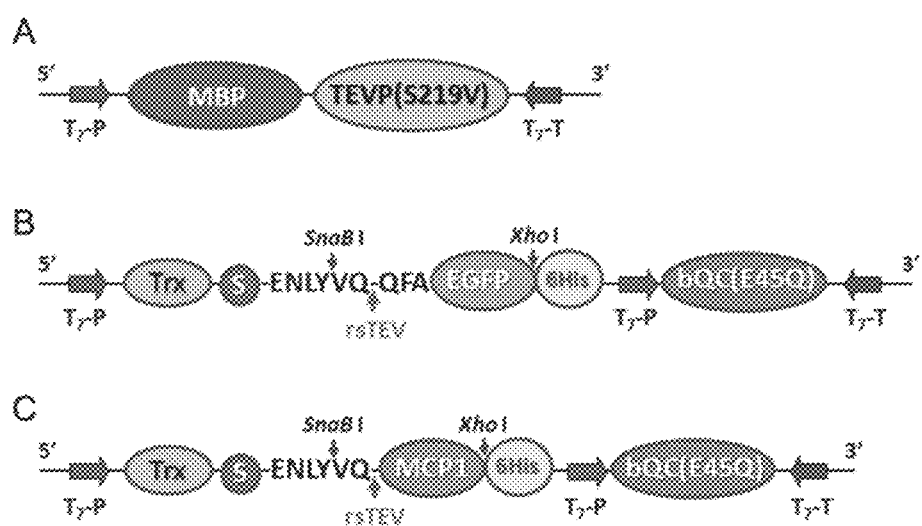
FIG. 1 are schematic diagrams that depict (A) pMBP-TEVP, (B) pTrx-rsTEV-$_{QF4}$EGFP-(His)$_6$-QC, and (C) pTrx-rsTEV-MCP1-(His)$_6$-QC, according to one example of the present disclosure.

In accordance with common practice, the various described features/elements are not drawn to scale but instead are drawn to best illustrate specific features/elements relevant to the present invention. Also, like reference numerals and designations in the various drawings are used to indicate like elements/parts.

DETAILED DESCRIPTION OF THE INVENTION

The detailed description provided below in connection with the appended drawings is intended as a description of the present examples and is not intended to represent the only forms in which the present example may be constructed or utilized. The description sets forth the functions of the example and the sequence of steps for constructing and operating the example. However, the same or equivalent functions and sequences may be accomplished by different examples.

For convenience, certain terms employed in the specification, examples and appended claims are collected here. Unless otherwise defined herein, scientific and technical terminologies employed in the present disclosure shall have the meanings that are commonly understood and used by one of ordinary skill in the art. Also, unless otherwise required by context, it will be understood that singular terms shall include plural forms of the same and plural terms shall include the singular. Specifically, as used herein and in the claims, the singular forms "a" and "an" include the plural reference unless the context clearly indicates otherwise. Also, as used herein and in the claims, the terms "at least one" and "one or more" have the same meaning and include one, two, three, or more.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in the respective testing measurements. Also, as used herein, the term "about" generally means within 10%, 5%, 1%, or 0.5% of a given value or range. Alternatively, the term "about" means within an acceptable standard error of the mean when considered by one of ordinary skill in the art. Other than in the operating/working examples, or unless otherwise expressly specified, all of the numerical ranges, amounts, values and percentages such as those for quantities of materials, durations of times, temperatures, operating conditions, ratios of amounts, and the likes thereof disclosed herein should be understood as modified in all instances by the term "about." Accordingly, unless indicated to the contrary, the numerical parameters set forth in the present disclosure and attached claims are approximations that can vary as desired. At the very least, each numerical parameter should at least be construed in light of the number of reported significant digits and by applying ordinary rounding techniques.

Definitions

"Nucleotide sequence", "polynucleotide" or "nucleic acid" can be used interchangeably and are understood to mean, according to the present disclosure, either a double-stranded DNA, a single-stranded DNA or products of transcription of said DNAs (e.g., RNA molecules). It should also be understood that the present disclosure does not relate to genomic polynucleotide sequences in their natural environment or natural state. The nucleic acid, polynucleotide, or nucleotide sequences of the invention can be isolated, purified (or partially purified), by separation methods including, but not limited to, ion-exchange chromatography, molecular size exclusion chromatography, or by genetic engineering methods such as amplification, subtractive hybridization, cloning, sub-cloning or chemical synthesis, or combinations of these genetic engineering methods.

The term "polypeptide" as used herein refers to a polymer of amino acids and does not refer to a specific length of the product; thus, peptides, oligopeptides, and proteins are included within the definition of polypeptide. This term also does not refer to or exclude post-translational modifications of the polypeptide, for example, glycosylation, acetylation, phosphorylation, sumoylation, cyclization, and the like. The term "polypeptide" includes fusion proteins, including, but not limited to, fusion proteins with a heterologous amino acid sequence, fusion proteins with heterologous and homologous leader sequences, and fusion proteins with or without a N-terminal or C-terminal modification.

The term "fusion protein" herein refers to a combination of two proteins or peptides joined in any manner or by any type of linkage, covalent, electrostatic, hydrophobic-interaction, affinity-type, or otherwise, that maintains the linkage between the partners, prevents cleavage of the linkage during the procedural steps that are followed in the practice of this invention, and leaves the binding characteristics of the protein substantially unchanged. A preferred kind of fusion protein for the purpose of this invention is a polypeptide made from a recombinant gene that contains portions of two or more different genes, the genes being joined so that their coding sequences are in the same reading frame, so that the genetic apparatus reads the gene fusion as a single gene. This type of fusion protein is also known as a hybrid protein or a chimeric protein.

The term "sequence identity" as used herein refers to the sequence relationships between two or more nucleic acids or amino acid sequences when aligned for maximum correspondence over a specified comparison window. The percentage of "identity" is determined by comparing two optimally aligned sequences over the comparison window. For "optimal alignment" of the two sequences, it will be appreciated that the portion of the sequence in the comparison window may include gaps (e.g., deletions or additions) as compared to the reference sequence, which does not contain additions or deletions. After alignment, the number of matched positions (i.e., positions where the identical nucleic acid base or amino acid residue occurs in both sequences) is determined and then divided by the total number of positions in the comparison window. This result is then multiplied by 100 to calculate the percentage of sequence or amino acid identity. In some embodiments, two sequences have the same total number of nucleotides or amino acids. The aligned sequences can be analyzed by any method familiar with one skilled artisan, including GAP, BESTFIT, BLAST, FASTA, and TFASTA.

The term "affinity chromatography matrix" or "AC matrix", as used herein, refers to a solid phase medium, typically a gel or resin, that allows for separation of biochemical mixtures based on a highly specific binding interaction between a protein of interest and the AC matrix, such as between a receptor and a ligand, an enzyme and a substrate, a metal ion and a tag protein, and an antigen and an antibody. Thus, the solid phase medium comprises a target to which the protein of interest is capable of reversibly affixing, depending upon the buffer conditions. Non-limiting examples of immobilized or solid phase media comprise the gel matrix, such as agarose beads, and the glass matrix, such as porous glass beads.

Expression System for Producing Pyroglutamate-Modified Proteins

As indicated above in the background section, the conventional method for producing the N-terminal pGlu-modified proteins requires a two-step reaction that is not only labor intensive, time-consuming, but also poor product yield. Accordingly, the present disclosure aims to provide an improved expression system and/or method, in which a target protein having a N-terminal pGlu modification is produced without the two-step reaction generally required in the conventional method, and accordingly a substantial increase in product yield.

The first aspect of the present invention is therefore directed to an expression system characterized in having two vectors for producing a target protein having a N-terminal pyroglutamate (pGlu) residue. The first vector is constructed to express a protein that may carry out intracellular self-cleavage of a fusion protein in the host, whereas the second vector is constructed to express the target protein, in which N-terminal cyclization is autonomously formed in the host.

According to preferred embodiments of the present disclosure, the present expression system comprises:

(a) a first vector comprising a first nucleotide sequence that encodes a first fusion protein, from the N-terminus to C-terminus, a maltose binding protein (MBP) and a tobacco etch virus protease (TEVP); and (b) a second vector comprising in sequence, (b-1) a second nucleotide sequence that encodes a second fusion protein, from the N-terminus to C-terminus, a thioredoxin (Trx), a S-tag, a linker having a TEVP recognition site (rsTEV) therein, the target protein, and a $(His)_6$-tag; and (b-2) a third nucleotide sequence that encodes a glutaminyl cyclase (QC) having a E45Q mutation;

wherein, the second nucleotide sequence is characterized in having two restriction endonuclease cleavage sites respectively located within the linker, and between the target protein and the $(His)_6$-tag; and the N-terminal pGlu residue of the target protein is autonomously formed in the host cell.

According to various embodiments of the preset disclosure, in the two vectors that are constructed, the first vector comprises a first nucleotide sequence encoding a first fusion protein, while the second vector comprises a second nucleotide sequence encoding a second fusion protein that comprises the desired target protein, and a third nucleotide sequences that encodes a glutaminyl cyclase (QC).

The first fusion protein encoded by the first nucleotide sequence contained in the first vector comprises the MBP and the TEVP, in which MBP acts as a carrier protein for enhancing the solubility of TEVP in the host. According to one embodiment of the present disclosure, the first nucleotide sequence is at least 90% identical to SEQ ID NO: 1, and the first fusion protein encoded thereof has an amino acid sequence at least 90% identical to SEQ ID NO: 5. Preferably, the TEVP in the present disclosure has a S219V mutation (i.e., TEVP (S219V)) that exhibits higher stability and cleavage efficiency, compared with wild-type TEVP.

The second fusion protein encoded by the second nucleotide sequence in the second vector comprises in sequence, i.e., from N-terminus to C-terminus, the Trx, the S-tag, the linker having a rsTEV therein, the target protein, and the $(His)_6$-tag.

According to various embodiments of the present disclosure, to generate the second fusion protein as indicated above, the second nucleotide sequence is designed to include two restriction endonuclease cleavage sites, so that any desired target sequence, such as the sequence that encodes the target protein, may be incorporated therein. In a typical example, two restriction endonuclease cleavage sites are respectively SnaB I, located within the sequence encoding the linker; and Xho I, located between the sequences encoding the target protein and the $(His)_6$-tag, respectively.

Further, a restriction site for TEVP (i.e., rsTEV) is also embedded in the second nucleotide sequence, so that the second fusion protein thus produced may subsequently be recognized and specifically cleaved by the 1EVP of the first fusion protein encoded by the first nucleotide sequence. In one example, the rsTEV has a sequence of ENLYVQQFA (SEQ ID NO: 29), and the cleavage site of TEVP is located between Gln-Gln. In another example, the rsTEV has a sequence of ENLYVQQPG (SEQ ID NO: 30), and the cleavage site of TEVP is located between Gln-Gln. In still another example, the rsTEV has a sequence of ENLYVQQ (SEQ ID NO: 31), and the cleavage site of TEVP is between Gln-Gln.

Target proteins that may be expressed by the present expression system are hormones, cytokines, chemokines, immunoglobulins, or ribonucleases. Examples of the chemokine include, but are not limited to, MCP1 and MCP2. Examples of the hormones include, but are not limited to, thyrotropin-releasing hormone (TRH), gonadotropin-releasing hormone (GRH), neurotensin, gastrin, and glucagon. Non-limiting examples of cytokines include, ANUP and IFN-γ. Examples of immunoglobulins include, but are not limited to, antibodies with a glutaminyl residue or a glutamyl residue on the N-terminus of light chain or heavy chain. Examples of the ribonucleases include, but are not limited to, frog ribonucleases, in which the frog is selected from the group consisting of *Rana pepeins*, *Rana japonica*, and *Rana catesbeana*.

According to one specific embodiment of the present disclosure, the target protein is EGFP, in which the second nucleotide sequence is at least 90% identical to SEQ ID NO: 2, and the second fusion protein encoded thereof comprising in sequence, the Trx, the S-tag, the linker having a rsTEV therein, the EGFP, and the $(His)_6$-tag, has an amino acid sequence at least 90% identical to SEQ ID NO: 6. According to another specific embodiment of the present disclosure, the target protein is MCP1, in which the second nucleotide sequence is at least 90% identical to SEQ ID NO: 3, and the second fusion protein encoded thereof comprising in sequence, the Trx, the S-tag, the linker with a rsTEV therein, the MCP1, and the $(His)_6$-tag, has an amino acid sequence at least 90% identical to SEQ ID NO: 7.

The third nucleotide sequence comprised in the second vector encodes the QC that catalyzes the cyclization of glutaminyl or glutamyl residue to form pGlu residue at the N-terminus of the target protein. Suitable example of QC that may be used in the present disclosure includes, but is not limited to, a QC derived from *Xanthomonas campestris*. According to one preferred embodiment of the present disclosure, the QC has a gain-of-function mutation at E45Q, which increases the protein activity. In one specific example, the third nucleotide sequence is at least 90% identical to SEQ ID NO: 4, and the QC with a E45Q mutation (i.e., QC(E45Q)) encoded thereof has an amino acid sequence at least 90% identical to SEQ ID NO: 8.

In practice, the first and second vectors are co-transduced into the host cell; so that the first fusion protein, the second fusion protein, and the QC are simultaneously expressed in the host cell. The TEVP of the first fusion protein would exhibit cleavage specificity toward the rsTEV sequence within the second fusion protein; accordingly two cleavage products are produced: one comprises the Trx and the S-tag fused to each other, while the other one comprises the target protein and the $(His)_6$-tag fused to each other. The glutaminyl or glutamyl residue at the N-terminus of the target protein is thus exposed, and can be further converted into the pGlu residue in a cyclization reaction catalyzed by QC. As known in the related art, the pGlu-modified proteins usually contain intra- and/or inter-molecular disulfide bridge that help maintaining the protein structure and function; Trx in the cleaved product acts as a redox protein to facilitate the correct formation of disulfide bond of the target protein. Accordingly, the thus produced target protein will not only have the desired N-terminal pGlu structure, but also the proper intra- and/or inter-molecular disulfide bonds. As to the $(His)_6$-tag, it is designed to endow the target protein with easy purification purpose. The $(His)_6$-tag at the end of the target protein exhibits binding specificity to various metal ions (e.g., nickel ion, cobalt ion, and copper ion) under specific conditions, and accordingly, the produced target protein with the $(His)_6$-tag at its C-terminus may be purified by affinity chromatography.

In general, any promoter commonly used in the field of molecular cloning may be employed to drive the expressions of the first and second fusion proteins, and the QC respectively encoded by the first, second and third nucleotide sequences in the first and second vectors. For example, the promoter can be any of T5, T7, tac, trc, lac, lacUV5, araBAD, or rhaBAD. In one preferred example, T7 promoter is employed in each of the first and second vector to drive the expressions of the first and second fusion proteins, as well as the QC.

According to some embodiments of the present disclosure, additional regulatory mechanism is provided in the first and second vectors, so as to enhance and/or control the production of the first fusion protein, the second fusion protein, and QC. Suitable regulatory mechanism includes, but is not limited to, lac operon (lactose operon), ara operon (L-arabinose operon, also known as araBAD operon) and trp operon (tryptophan operon). In one example, three lac operators are respectively placed down-stream of the first, second, and third promoters, and accordingly, the expressions of the first and second fusion proteins, and the QC can be regulated by Isopropyl β-D-1-thiogalactopyranoside (IPTG).

Examples of suitable host cell for use with the present expression system include, but are not limited to, *Escherichia coli* (*E. coli*) cell, *Corynebacterium glutamicum* (*C. glutamicum*) cell, and *Pseudomonas fluorescens* (*P. fluorescens*) cell. According to preferred embodiments of the present disclosure, the host cell is an *E. coli* cell. In one working example, the host cell is *E. coli* strain BL21 cell; while in another example, the host cell is *E. coli* strain Origami B cell.

Accordingly, in the embodiments of the present disclosure, the first fusion protein, the second fusion protein, and the QC(E45Q) are simultaneously expressed in the *E. coli* cell; and the target protein (e.g., EGFP or MCP1), which comprises a pGlu at the N-terminus and a $(His)_6$-tag at the C-terminus, is autonomously formed therein.

Method of Producing Pyroglutamate-Modified Proteins

A further aspect of the present disclosure is directed to a method for producing a target protein having a N-terminal pGlu residue in a host cell by use of the expression system described above. The method comprises:

(a) transducing the host cell with the present expression system;

(b) cultivating the transduced host cell of step (a) in a culture medium;

(c) lysing the cultivated host cell of step (b); and (d) purifying the target protein from the supernatant of the lysed product of step (c) by affinity chromatography.

In step (a), the present expression system as described above is transduced into the host cell by any method familiar by any skilled artisan in the related art, which includes, but is not limited to, viral infection (e.g., bacteriophage), electroporation, liposome-mediated transformation, heat-shock treatment, and exposure to chemicals such as calcium ions, and polyethylene glycol. Either method is aimed to render the host cell competent to foreign DNA(s). According to one specific embodiment, the present expression system is transduced into the host cell by the heat-shock treatment. Specifically, the host cell is first cultured in a calcium-rich environment to counteract the electrostatic repulsion between the vector DNA(s) and the membrane of host cell, then a sudden increase in temperature is introduced so as to create pores in the membrane that allow the entry of vector DNA(s) into the host cell.

Non-limiting examples of the host cell suitable used with the present expression system include, *Escherichia coli* (*E. coli*) cell, *Corynebacterium glutamicum* (*C. glutamicum*) cell, and *Pseudomonas fluorescens* (*P. fluorescens*) cell. According to preferred embodiments of the present disclosure, the host cell is an *E. coli* cell. In one working example, the host is *E. coli* strain BL21 cell; while in another example, the host is *E. coli* strain Origami B cell.

In step (b), the transduced host cell of step (a) is cultured in a suitable culture medium so as to allow the multiplication and/or growth of the transduced host cell. In the case when *E. coli* is used as the host, a lysogeny broth (LB, also known as luria broth, lennox broth, or luria-bertani medium) is employed as the culture medium. According to some embodiments of the present disclosure, each of the first, second, and third promoters in the first and second vectors is controlled by a lac operator, and thus, the expressions of the first and second fusion proteins, and the QC can be induced by the addition of IPTG in the cultured medium.

In step (c), the host cell is lysed to allow subsequent purification of the target protein. The host cells may by lysed by physical disruption, which includes, but is not limited to, liquid homogenization, sonication, freeze and thaw, and manually grinding; and/or chemical disruption, such as treatment with the hypotonic buffer supplemented with lysozyme, DNase, and/or nuclease. In one specific embodiment of the present disclosure, the host cell is lysed by physical disruption, which is exerted by a cell disrupter. It is worth noting that the target protein (i.e., EGFP or MCP1) produced by the present expression system is expressed in the soluble fraction of the host cell; accordingly, there is no need to perform additional steps commonly required for extracting an insoluble protein (e.g., protein denaturation and folding), thus may substantially increase the production efficiency and product yield.

In step (d), the target protein is purified by affinity chromatography based on the binding affinity between the $(His)_6$-tag and metal ions. Specifically, the metal ions (e.g., nickel ion, cobalt ion, and copper ion) are first immobilized on a solid support (e.g., resin beads of a column); then, allow the $(His)_6$-tag-comprised protein to flow pass the support in a proper buffer condition and flow rate, so that the $(His)_6$-tag can bind to the immobilized metal ions. The column is then eluted with imidazole, known as a competitive agent, to disrupt the binding between $(His)_6$-tag and metal ions, and thus, the separation of the target protein and the immobilized metal ions. According to one preferred embodiment, the target protein is purified by a column immobilized thereon with nickel ions. Since the purification relies on the binding of the (His)$_6$-tag with the metal ions, both the second fusion protein (comprising in sequence, the Trx, the S-tag, the linker with the rsTEV therein, the target protein and the (His)$_6$-tag), and the cleavage product thereof (comprising the target protein and the (His)$_6$-tag), might be simultaneously eluted. Accordingly, the eluted products are further selected by a size-exclusion chromatography (SEC), based on the size differences between the second fusion protein and the cleavage product thereof. In one preferred embodiment, SEC is exerted by a Superdex-75 column.

The present method is useful for the expression of a target protein having pGlu modification at its N-terminus. Suitable examples of the target protein include, but are not limited to, hormone, cytokine, chemokine, immunoglobulin, and ribonuclease. In some embodiments, the chemokine is MCP1 or MCP2; the hormone is thyrotropin-releasing hormone, gonadotropin-releasing hormone, neurotensin, gastrin, or glucagon; the cytokine is ANUP or IFN-γ; the immunoglobulin is an antibody with a glutaminyl residue or a glutamyl residue on the N-terminus of light chain or heavy chain; the ribonuclease is a frog ribonuclease, in which the frog may be selected from the group consisting of *Rana pepeins, Rana japonica*, and *Rana catesbeana*. In one specific example, the present method is used to express and produce the active target protein MCP1.

The following Examples are provided to elucidate certain aspects of the present invention and to aid those of skilled in the art in practicing this invention. These Examples are in no way to be considered to limit the scope of the invention in any manner. Without further elaboration, it is believed that one skilled in the art can, based on the description herein, utilize the present invention to its fullest extent. All publications cited herein are hereby incorporated by reference in their entirety.

EXAMPLES

Materials and Methods

Production and Purification of Target Protein

The host cell *E. coli* strains BL21-CondonPlus(DE3)-RIL (Stratagene) and Origami B (Novagen) were respectively used to express EGFP and monocyte chemoattractant proteins (MCPs). To culture Origami B cells, the LB medium containing ampicillin (70 mg/ml) and kanamycin (30 mg/ml) was used, while the LB medium containing antibiotic chloramphenicol (34 mg/ml) was employed for culturing BL21-CondonPlus(DE3)-RIL. The cultures were grown overnight at 37° C. until OD$_{600}$ reached about 0.6, and then induced with 1 mM IPTG at 18-20° C. for 24 h. The cells were harvested by centrifugation at 6,000 g and the cell pellets were suspended in 100 ml buffer A (250 mM NaCl in 50 mM Tris-HCl, pH 7.5). The cell suspension was lysed by using a cell disrupter (Constant Systems), and the cell lysate was clarified by centrifugation at 90,000 g for 40 min. Subsequently, the supernatant was loaded onto a column packed with Ni-NTA resin (GE Healthcare) pre-equilibrated with buffer A. The column was washed with 40-column volume of buffer A and eluted with a linear gradient of 10-100% buffer B (500 mM imidazole and 250 mM NaCl in 50 mM Tris-HCl, pH 7.5). The fractions containing (His)$_6$-tag fusion proteins were pooled and then dialyzed against buffer C (150 mM NaCl in 20 mM Tris-HCl, pH 8.0) to remove imidazole.

The produced (His)$_6$-tag-comprised fusion proteins were further purified by using a Superdex-75 column so as to isolate the fusion protein with molecular weight between 3,000 and 70,000. The purity of the fusion proteins was judged by SDS-PAGE analysis stained with coomassie blue.

NanoESI-Q/TOF MS Analysis

The $_{QF4}$-EGFP, MCPs, and trypsin solutions were prepared in aqueous ammonium bicarbonate buffer (25 mM, pH 8.5). The solutions of $_{QF4}$-EGFP and MCPs (approximately 1 mg) were reduced with DTT at 37° C. for 1 h first, and then alkylated with iodoacetamide at 37° C. for another 1 h. The in-solution digestion was carried out by adding trypsin at an enzyme-to-substrate molar ratio of 1:50 at 37° C. for 16 h. The digested products were diluted with 0.1% formic acid to a concentration of 0.1 pmol/ml, and the peptide mixtures were desalted using a C18 Ziptip (Millipore). The resulting peptides were evaporated to dryness using a SpeedVac.

The intact masses of modified and unmodified $_{QF4}$-EGFP and MCP1 were determined by direct infusion on the QSTAR-XL hybrid quadrupole time-of-flight mass spectrometer (Applied Biosystems/MDS Sciex, Toronto, Canada) equipped with a home-made nanosprayer applied with 23.5 kV. After incubation, samples (5 ml) were mixed with 100 ml of 50% acetonitrile/0.1% formic acid and infused into the mass spectrometer at a flow rate of 300 nl/min. Each sample was analyzed in full scan mode using a m/z 400-2,000 mass range, and the raw mass spectra were de-convoluted using Analyst QS 1.1 protein deconvolution software. The instrument was calibrated using the fragment ions resulting from the collision-induced dissociation (CID) of Glu-fibrinopeptide B (Sigma). The mass accuracy of full mass range was better than 50 ppm.

NanoLC-MS/MS Analysis

Dried peptides were dissolved in 5% acetonitrile and 0.1% formic acid, and 5 ml of the solution was loaded onto a 75-μm×250-mm nanoACQUITY UPLC BEH130 column packed with C18 resin (Waters, Milford USA). The peptides mixtures were separated by online nanoflow liquid chromatography using nanoAcquity system (Waters, Milford, Mass.) with a linear gradient of 5 to 50% acetonitrile (in 0.1% formic acid) in 95 min, followed by a sharp increase to 85% acetonitrile in 1 min and held for another 13 min at a constant flow rate of 300 nl/min. Peptides were detected in an LTQ-Orbitrap Velos hybrid mass spectrometer (Thermo Scientific) using a data-dependent CID Top20 method in positive ionization mode. For each cycle, full-scan MS spectra (m/z 350-1,600) were acquired in the Orbitrap at 60,000 resolution (at m/z 400) after accumulation to a target intensity value of 5×10$^6$ ions in the linear ion trap. The 20 most intense ions with charge states ≥2 were sequentially isolated to a target value of 10,000 ions within a maximum injection time of 100 ms and fragmented in the high-pressure linear ion trap by low-energy CID with normalized collision energy of 35%. The resulting fragment ions were scanned out in the low-pressure ion trap at the normal scan rate and recorded with the secondary electron multipliers. Ion selection threshold was 500 counts for MS/MS, and the selected ions were excluded from further analysis for 90 s. An activation q=0.25 and activation time of 10 ms were used. Standard mass spectrometric conditions for all experiments were: spray voltage, 1.9 kV; no sheath and auxiliary gas flow; heated capillary temperature, 200° C.; predictive automatic gain control (AGC) enabled, and an S-lens RF level of 60%.

Cell Migration Assay

U937 cells were purchased from the American Type Cell Collection. The cells at 2-3×10$^6$ cells/ml were grown in RPMI 1640 medium (GIBCO) supplemented with 10% heat-inactivated fetal bovine serum (GIBCO). Fresh U937 cells were then incubated with 10 mM Calcein AM (BD Biosciences) at 37° C. for 1 h with 5% humidified $CO_2$. Subsequently, an aliquot of U937 cells (about $1\times10^6$ cells/ml) suspended in serum-free RPMI 1640 medium was added to the upper compartment of the 24-well BD Falcon HTS FluoroBlok Inserts (BD Biosciences). This apparatus has a polyethylene terephthalate (PET) membrane (8 mm pore size) that blocks the transmission of light from 490 to 700 nm. This allows detection of cells present in the lower compartment only. The cells were allowed to migrate into the lower compartment at 37° C. for 2 h in the presence of $_{pE}$-MCL1-(His)$_6$, with the recombinant Q-MCP1 (Pepro-Tech) as a negative control. Once cells migrate through the pores of the PET membrane, they are no longer shielded from the light and can be detected by a fluorescence plate reader (Bio-Tek-Synergy HT Microplate Reader, Bio-Tek Instruments). Chemotactic index (CI) was calculated from the cell migration activity towards chemoattractant divided by the migration activity in the absence of chemoattractant. The CI values, shown as mean±SEM, were calculated from five independent experiments.

Example 1 Production of N-Terminal pGlu-Modified EGFP

The efficacy of the present expression system in producing a pGlu-modified protein was tested in the present example, in which EGFP was employed as a target protein. To this purpose, two expression vectors were respectively constructed, so that a first fusion protein MBP-TEVP, a second fusion protein Trx-rsTEV-EGFP-(His)$_6$, and QC(E45Q) were produced.

1.1 Plasmid Construction 1.1.1 Construction of pMBP-TEVP

The first expression vector pMBP-TEVP was constructed by amplifying the DNA segments encoding MBP-TEVP (S219V) from the plasmid pMBP-TEVP (Yan-Ping Shin et al, Self-cleavage of fusion protein in vivo using TEV protease to yield native protein, Protein Science 2005, p 936-941) by PCR with a forward primer of SEQ ID NO: 9 or 10, and a reverse primer of SEQ ID NO: 11 or 12. The amplified product was then constructed into the plasmid pRSF-1b (Novagen) by restriction enzymes Nco I and Sal I so as to produce the expression vector pMBP-TEVP (FIG. 1A); in which the promoter is a T7 promoter with one lac operator located down-stream thereof, and thus, the expression of the first fusion protein MBP-TEVP can be regulated by IPTG.

The produced expression vector pMBP-TEVP comprised a nucleotide sequence of SEQ ID NO: 1, and the fusion protein MBP-TEVP encoded thereof had an amino acid sequence of SEQ ID NO: 5.

1.1.2 Construction of pTrx-rsTEV-$_{QFA}$EGFP-(his)$_6$-QC(E45Q)

To produce the expression vector, pTrx-rsTEV-$_{QFA}$EGFP-(His)$_6$-QC(E45Q), DNA segment encoding EGFP was amplified from the plasmid pMBP-rsTEV-EGFP (Yan-Ping Shin et al, Self-cleavage of fusion protein in vivo using TEV protease to yield native protein, Protein Science 2005, p 936-941) by PCR using primers of SEQ ID NOs: 13 and 14, and DNA segment encoding QC(E45Q) was amplified from the expression vector that comprised the gene encoding QC(E45Q) (Wei-Lin Huang et al, Crystal structure and functional analysis of the glutaminyl cyclase from Xanthomonas campestris, Journal of molecular biology 2010, p 374-388) by PCR using primers of SEQ ID NOs: 15 and 16, in which QC(E45Q) is a gain-of-function mutant. The amplified DNA segments were then annealed with the LIC Duet Minimal Adaptor (Novagen) by a post-PCR processing step, in which the adaptor comprised a T7 promoter, a lac operon, a ribosome binding sequence (rbs), and a start codon. Specifically, the adaptor was designed to possess asymmetric, GC-rich 12-based overhangs on each end, in which the 5'-end overhang sequence was complementary to the 3'-end of the amplified DNA segment encoding EGFP, while the 3'-end overhang sequence was complementary to the 5'-end of the amplified DNA segment encoding QC(E45Q). Accordingly, the EGFP-encoding DNA segment, the adaptor, and the QC(E45Q)-encoding DNA segment could be annealed based on those complementary sequences. The annealed EGFP-adaptor-QC(E45Q) was then constructed into the plasmid pET-32Ek-LIC (Novagen) so as to produce the vector pTrx-rsTEV-EGFP-(His)$_6$-QC(E45Q), which comprised in sequence: a first T7 promoter, a first lac operon, a first nucleotide sequence that encoded Trx, rsTEV, and EGFP, a second T7 promoter, a second lac operon, and a second nucleotide sequence that encoded QC(E45Q). Accordingly, the expressions of fusion protein Trx-rsTEV-EGFP and QC(E45Q) were respectively driven by a T7 promoter and could be regulated by IPTG.

To generate EGFP that lacks a glutaminyl or a glutamyl residue at its N-terminus, three additional amino acids QFA were inserted to the N-terminus of EGFP by site-directed mutagenesis using primers of SEQ ID NOs: 17 and 18, so that they acted as the substrate of QC in the cyclization reaction. The produced vector designated as pTrx-rsTEV-$_{QFA}$EGFP-(His)$_6$-QC(E45Q) (FIG. 1B) comprised a first nucleotide sequence of SEQ ID NO: 2, which encoded the fusion protein Trx-rsTEV-$_{QFA}$EGFP-(His)$_6$ having an amino acid sequence of SEQ ID NO: 6, and a second nucleotide sequence of SEQ ID NO: 4, which encoded the protein QC(E45Q) having an amino acid sequence of SEQ ID NO: 8.

1.1.3 Construction of pTrx-rsTEV-$_{QPG}$EGFP-(his)$_6$-QC(E89A)

The expression vector pTrx-rsTEV-$_{QPG}$EGFP-(His)$_6$-QC(E89A) was constructed by the similar method as described in example 1.1.2. Briefly, the DNA segment encoding EGFP was amplified by the method illustrated in example 1.1.2, and the DNA segment encoding QC(E89A) was amplified from the expression vector that comprised the gene encoding QC(E89A) (see Wei-Lin Huang et al, Crystal structure and functional analysis of the glutaminyl cyclase from Xanthomonas campestris, Journal of molecular biology 2010, p 374-388) by PCR using primers of SEQ ID NOs: 15 and 16, in which QC(E89A) is a loss-of-function mutant. The amplified DNA segments were then annealed with the LIC Duet Minimal Adaptor (Novagen) and constructed into the plasmid pET-32Ek-LIC (Novagen) so as to produce the vector pTrx-rsTEV-EGFP-(His)$_6$-QC(E89A).

In this example, another three amino acids, i.e., QPG, were inserted to the N-terminus of EGFP via a site-directed mutagenesis by the use of primers of SEQ ID NOs: 19 and 20. The produced plasmid designated pTrx-rsTEV-$_{QPG}$EGFP-(His)$_6$-QC(E89A) comprised a first nucleotide sequence of SEQ ID NO: 21, which encoded the fusion protein Trx-rsTEV-$_{QPG}$EGFP-(His)$_6$ having an amino acid sequence of SEQ ID NO: 22, and a second nucleotide sequence of SEQ ID NO: 26, which encoded the protein QC(E89A) having an amino acid sequence of SEQ ID NO: 27.

1.2 Characterization of pGlu Formation at the N-Terminus of EGFP

In this example, the expression vectors pMBP-TEVP of example of 1.1.1 and pTrx-rsTEV-$_{QFA}$EGFP-(His)$_6$-QC (E45Q) of example 1.1.2 were co-transfected into *E. coli* BL21-CondonPlus(DE3)-RIL, followed by the addition of 1 mM of IPTG in the culture medium; the entire culture were then cultivated at 18-20° C. for 1 h. The *E. coli* cells were lysed and the supernatant was collected therefrom by centrifugation at 90,000 g that was then analyzed by western blot.

Figure 2A:
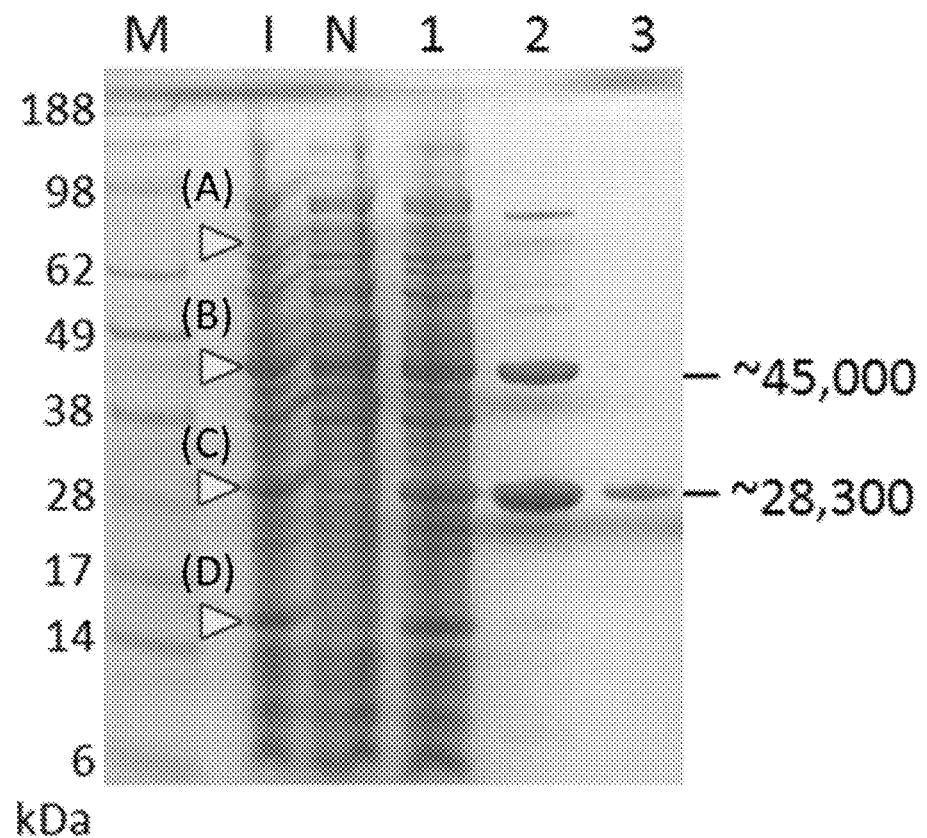
FIG. 2A is a photograph of sodium dodecyl sulfate polyacrylamide gel electrophoresis (SDS-PAGE) that depicts the proteins extracted from *E. coli* co-transfected with pMBP-TEVP and pTrx-rsTEV-$_{QF4}$EGFP-(His)$_6$-QC, in which lane M presents the protein marker, lane I presents the proteins of *E. coli* induced with Isopropyl β-D-1-thiogalactopyranoside (IPTG), land N presents the proteins of *E. coli* without IPTG induction, land 1 presents the soluble fraction of proteins extracted from *E. coli* induced with IPTG, lane 2 presents the fusion proteins Trx-rsTEV-EGFP-(His)$_6$ and EGFP-(His)$_6$ that are extracted from *E. coli* induced with IPTG followed by purification via Ni-NTA column, lane 3 presents the fusion protein EGFP-(His)$_6$ that is extracted from *E. coli* induced with IPTG followed by purification via Ni-NTA column and Superdex-75 column, in which arrow head (A) indicates the fusion protein MBP-TEVP (about 73 kDa), arrow head (B) indicates the fusion protein Trx-rsTEV-EGFP-(His)$_6$ (about 45 kDa), arrow head (C) indicates QC and/or the fusion protein EGFP-(His)$_6$ (about 28-30 kDa), and arrow head (D) indicates the cleavage product Trx-rsTEV (about 15 kDa), according to one example of the present disclosure.

As depicted in FIG. 2A, compared to the control (i.e., lane N), the expression of both the fusion protein Trx-rsTEV-$_{QF4}$EGFP-(His)$_6$ (SEQ ID NO: 6, molecular weight of 45 kDa), and the fusion protein MBP-TEVP (SEQ ID NO: 5, molecular weight of 73 kDa), were induced by the addition of IPTG in *E. coli* (lane I). Further, both the fusion proteins were mainly detected in the soluble fraction of *E. coli* (lane 1). The protein bands appeared to contain proteins with various molecular weights, including the induced QC(E45Q) (SEQ ID NO: 8, molecular weight of about 30 kDa), and the cleaved product EGFP-(His)$_6$ (about 28 kDa). Further analysis on the expressed proteins by affinity column revealed that more than 50% of Trx-rsTEV-$_{QF4}$EGFP-(His)$_6$ was successfully cleaved by TEVP to yield EGFP-(His)$_6$ (lane 2); and the fusion protein EGFP-(His)$_6$ was eventually separated from Trx-rsTEV-$_{QF4}$EGFP-(His)$_6$ by a Superdex-75 column (lane 3).

Figure 2B:
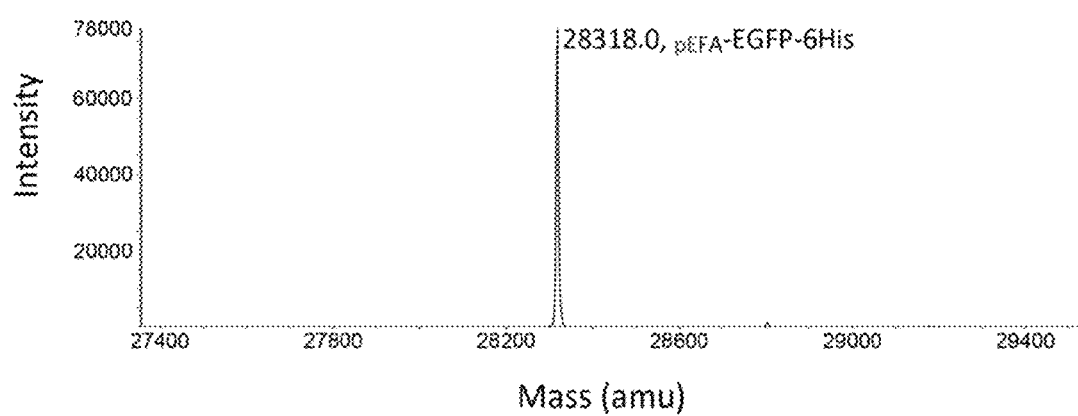
FIG. 2B is a result of NanoESI-Q/TOF MS analysis that depicts the fusion protein EGFP-(His)$_6$ extracted from *E. coli* co-transfected with pMBP-TEVP and pTrx-rsTEV-$_{QF4}$EGFP-(His)$_6$-QC, according to one example of the present disclosure.
Figure 2C:
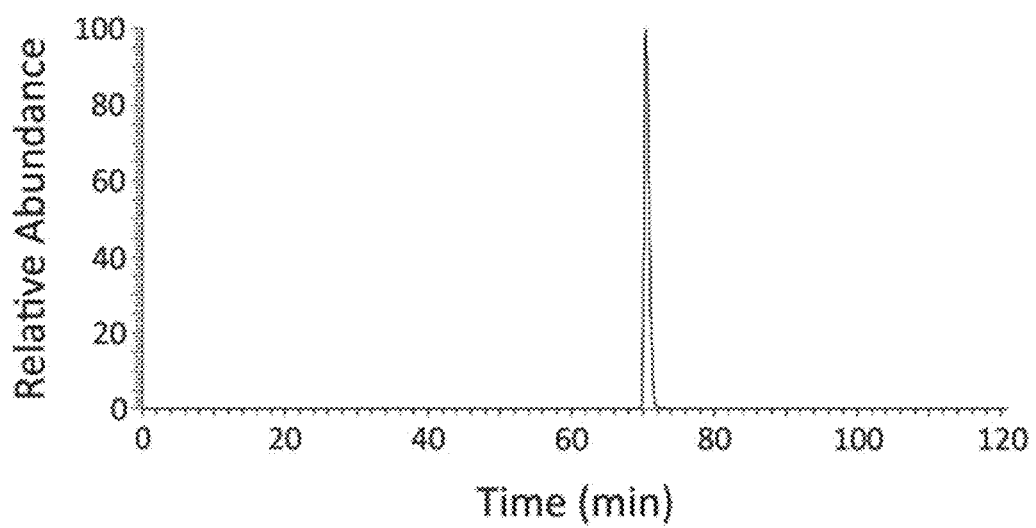
FIG. 2C is a result of NanoLC-MS/MS analysis that depicts the fusion protein EGFP-(His)$_6$ extracted from *E. coli* co-transfected with pMBP-TEVP and Trx-rsTEV-$_{QF4}$EGFP-(His)$_6$-QC, according to one example of the present disclosure.

The isolated protein EGFP-(His)$_6$ was then subjected to nanoESI-Q/TOF MS so as to evaluate the cyclization efficiency. As illustrated in FIG. 2B, the spectra in the mass range of EGFP-(His)$_6$ exhibited a single signal that corresponded to the mass of $_{pEF4}$-EGFP-(His)$_6$ ($M_r$=28,318.0 amu), in which pE represented pGlu, and no signal was detected for the un-cyclized $_{QF4}$-EGFP-(His)$_6$ ($M_r$=28,335.1 amu). The data indicated that all the Gln residues at the N-terminus of EGFP had been cyclized into the pGlu residue. The purified EGFP-(His)$_6$ was further digested with trypsin and then subjected to nanoLC-MS/MS analysis to identify the N-terminal residues. As depicted in FIG. 2C, only one species of N-terminal fragment with pGlu formation was identified.

Figure 2D:
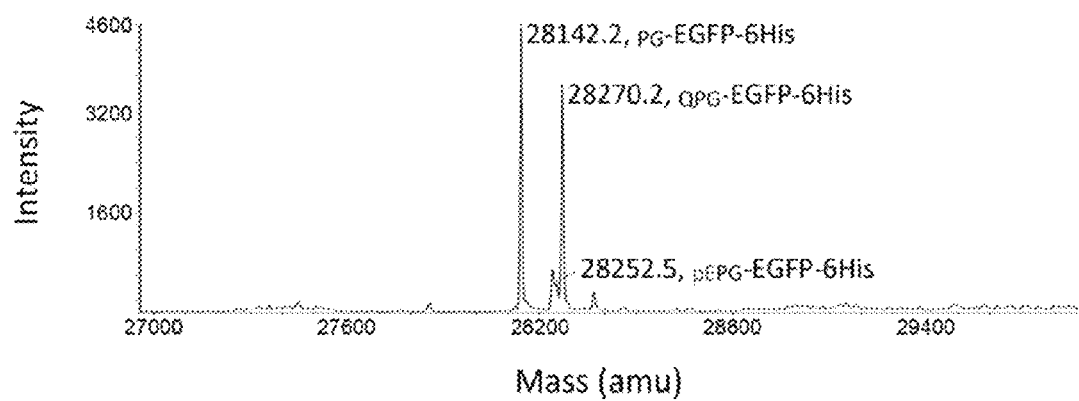
FIG. 2D is a result of NanoESI-Q/TOF MS analysis that depicts the fusion protein EGFP-(His)$_6$ extracted from *E. coli* co-transfected with pMBP-TEVP and pTrx-rsTEV-$_{QF4}$EGFP-(His)$_6$-QC, in which QC is a loss-of-function mutant QC(E89A), according to one example of the present disclosure.

To confirm the role of QC in the N-terminal pGlu formation, the vector pMBP-TEVP of example 1.1.1 and the vector pTrx-rsTEV-$_{QPG}$EGFP-(His)$_6$-QC(E89A) of example 1.1.3 were co-transfected into *E. coli* BL21-CondonPlus(DE3)-RIL, and the fusion protein EGFP-(His)$_6$ was isolated by similar procedures as described above. As illustrated in FIG. 2D, the mass spectra exhibited a first signal that corresponded to $_{PG}$-EGFP-(His)$_6$ ($M_r$=28,142.2 amu) and a second signal that corresponded to $_{QPG}$-EGFP-(His)$_6$ ($M_r$=28,270.2 amu); in which the $_{QPG}$-EGFP-(His)$_6$ was degraded by *E. coli* aminopeptidase to form $_{PG}$-EGFP-(His)$_6$. Compared with $_{QPG}$-EGFP-(His)$_6$ or $_{PG}$-EGFP-(His)$_6$, a very weak signal corresponding to $_{pEPG}$-EGFP-(His)$_6$ ($M_r$=28,252.5 amu) was also detected. Thus, in the absence of functional QC, most EGFP-(His)$_6$ remained in their un-cyclized forms.

The above data indicated that the present expression system can be used to efficiently produce the EGFP with an N-terminal pGlu modification.

Example 2 Production of N-Terminal pGlu-Modified MCP1

The efficacy of the present expression system in producing a pGlu-modified protein was further tested in a physiological QC substrate, MCP1.

2.1 Construction of pTrx-rsTEV-MCP1-(his)$_6$-QC(E45Q)

The pTrx-rsTEV-MCP1-(His)$_6$-QC(E45Q) was constructed in a similar manner according to procedures described in example 1.1.2, except MCP1 was employed as the target protein. Specifically, DNA segment encoding MCP1 was amplified from the nucleotide sequence of SEQ ID NO: 28 by PCR using a forward primer of SEQ ID NO: 23 and a reverse primer of SEQ ID NO: 24 or 25; the amplified DNA segment comprised an 3'-end nucleotide sequence that was complementary to the 5'-end overhang sequence of the LIC Duet Minimal Adaptor (Novagen). As described in example 1.1.2, the DNA segment encoding QC(E45Q) amplified by primers of SEQ ID NOs: 15 and 16 comprised a 5'-end nucleotide sequence that was complementary to the 3'-end overhang sequence of the LIC Duet Minimal Adaptor (Novagen). Accordingly, the DNA segment encoding MCP1, the adaptor, and the DNA segment encoding QC(E45Q) could be annealed together followed by constructing into the plasmid pET-32Ek-LIC (Novagen) so as to produce the vector pTrx-rsTEV-MCP1-(His)$_6$-QC (E45Q) (FIG. 1C). With the similar structure as the expression vector of example 1.1.2, the produced vector comprised two nucleotide sequences that were respectively driven by a T7 promoter and regulated by IPTG; one of which had the sequence of SEQ ID NO: 3, and the fusion protein Trs-rsTEV-MCP1 encoded thereof had an amino acid sequence of SEQ ID NO: 7; another nucleotide sequence had the sequence of SEQ ID NO: 4, and the protein QC(E45Q) encoded thereof had an amino acid sequence of SEQ ID NO: 8.

2.2 Characterization of pGlu Formation at the N-Terminus of MCP1

With the similar step described in example 1.2, the expression vectors pMBP-TEVP of example 1.1.1 and pTrx-rsTEV-MCP1-(His)$_6$-QC(E45Q) of example 2.1 were co-transfected into *E. coli* Origami B followed by the addition of 1 mM of IPTG in the culture medium so as to induce the protein expression; the expressed protein was collected from the supernatant of cell lysate and analyzed by western blot.

Figure 3A:
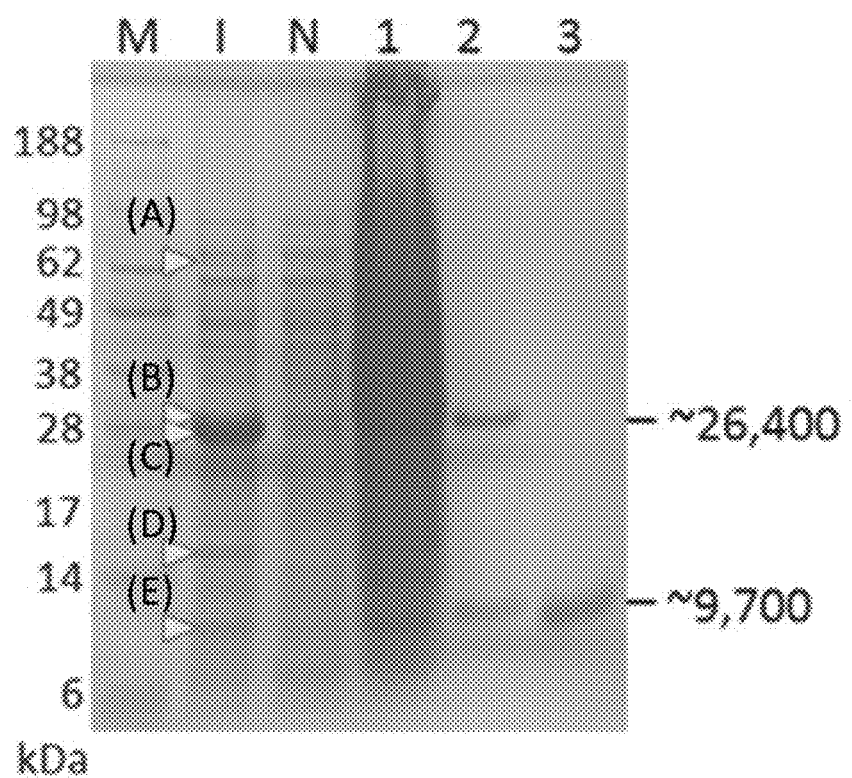
FIG. 3A is a photograph of SDS-PAGE that depicts the proteins extracted from *E. coli* co-transfected with pMBP-TEVP and pTrx-rsTEV-MCP1-(His)$_6$-QC, in which lane M presents the protein marker, lane I presents the proteins of *E. coli* induced with IPTG, land N presents the proteins of *E. coli* without IPTG induction, land 1 presents the soluble fraction of proteins extracted from *E. coli* induced with IPTG, lane 2 presents the fusion proteins Trx-rsTEV-MCP1-(His)$_6$ and MCP1-(His)$_6$ that are extracted from *E. coli* induced with IPTG followed by purification via Ni-NTA column, lane 3 presents the fusion protein MCP1-(His)$_6$ that is extracted from *E. coli* induced with IPTG followed by purification via Ni-NTA column and Superdex-75 column, in which arrow head (A) indicates the fusion protein MBP-TEVP (about 73 kDa), arrow head (B) indicates QC (about 30 kDa), arrow head (C) indicates the fusion protein Trx-rsTEV-MCP1-(His)$_6$ (about 26.4 kDa), arrow head (D) indicates the cleavage product Trx-rsTEV (about 15 kDa), and arrow head (E) indicates the fusion protein MCP1-(His)$_6$ (about 9.7 kDa), according to the another example of the present disclosure.

As illustrated in FIG. 3A, compared to the control (i.e., lane N), the fusion protein Trx-rsTEV-MCP1-(His)$_6$ (SEQ ID NO: 7, molecular weight of 26 kDa) could be induced by IPTG in *E. coli* (lane I). Notably, it was mainly detected in the soluble fraction of *E. coli* (lane 1) so that the protein could be easily and efficiently purified from the supernatant of the cell lysate followed by purification via the affinity column. The analysis result indicated that about 40% of Trx-rsTEV-MCP1-(His)$_6$-QC(E45Q) was cleaved by TEVP to produce MCP1-(His)$_6$ (molecular weight of 9.7 Da, lane 2). Further, the cleaved fusion protein MCP1-(His)$_6$ could be specifically purified by a Superdex-75 column (lane 3).

Figure 3B:
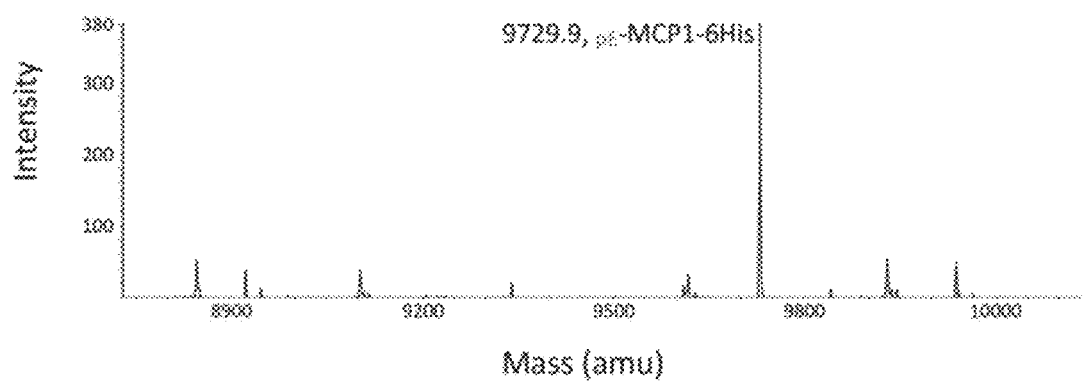
FIG. 3B is a result of NanoESI-Q/TOF MS analysis that depicts the fusion protein MCP1-(His)$_6$ extracted from *E. coli* co-transfected with pMBP-TEVP and pTrx-rsTEV-MCP1-(His)$_6$-QC, according to another example of the present disclosure.
Figure 3C:
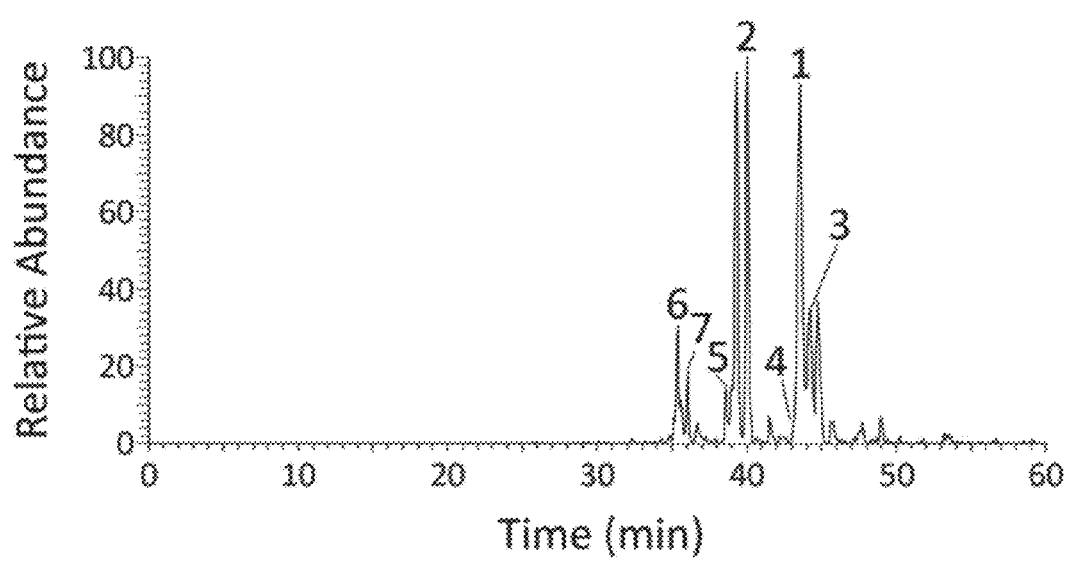
FIG. 3C is a result of NanoLC-MS/MS analysis that depicts the fusion protein MCP1-(His)$_6$ extracted from *E. coli* co-transfected with pMBP-TEVP and pTrx-rsTEV-MCP1-(His)$_6$-QC, according to another example of the present disclosure.

The purified MCP1-(His)$_6$ was subjected to nanoESI-Q/TOF MS. As illustrated in FIG. 3B, the mass spectra in the range of MCP1-(His)$_6$ exhibited a single signal corresponding to $_{pE}$-MCP1-(His)$_6$ ($M_r$=9,729.9 amu), in which pE represented pGlu, and no signal was detected for the un-cyclized $_Q$-MCP1-(His)$_6$. Meanwhile, the purified MCP1-(His)$_6$ was digested with trypsin and then subjected to nanoLC-MS/MS analysis to identify the N-terminal residues. As depicted in FIG. 3C, several signals were detected for different levels of modification at the N-terminus of MCP1. However, further analysis indicated that the fragments with a N-terminal pGlu reside (i.e., peaks 1-4) is about 4.9-fold higher than the fragments with an un-cyclized N-terminus (i.e., peaks 5-7). The result suggested that most of the N-terminal Gln residues of MCP1 had been cyclized to the pGlu residue.

Thus, the data demonstrated that the present expression system can be used to produce a physiological protein (such as MCP1) having a pGlu-modification at its N-terminus.

2.3 Evaluation of the Cellular Activity of MCP1

Figure 4:
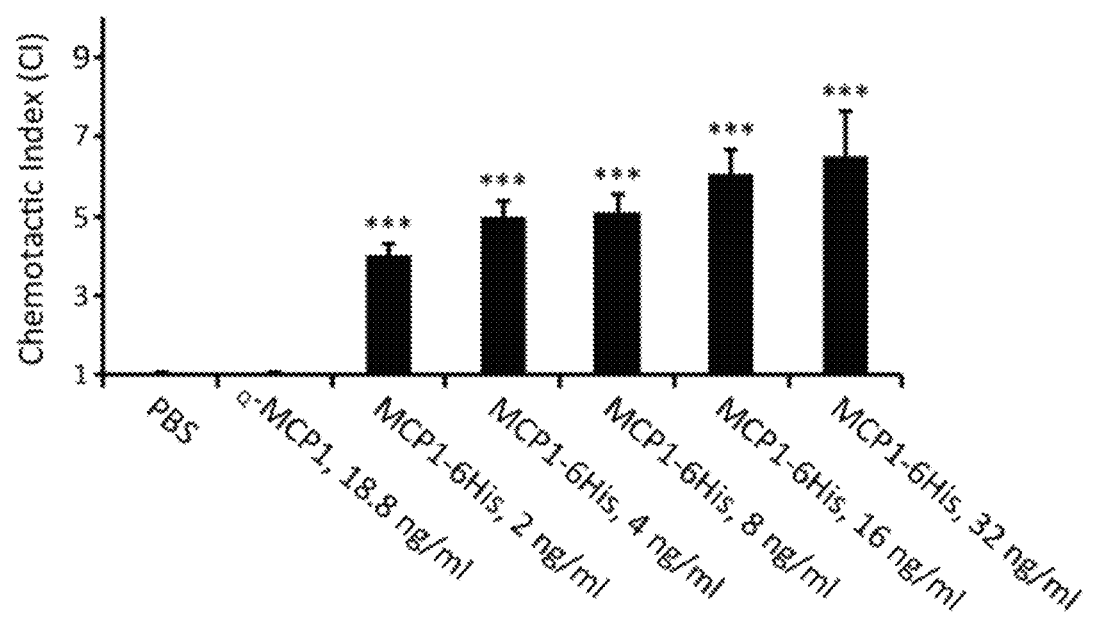
FIG. 4 is a histogram that depicts the activity of U937 cells respectively treated with specified concentrations of fusion protein MCP1-(His)$_6$, and $_Q$-MCP1, which serves as a negative control, according to one example of the present disclosure.

The cellular activity of fusion protein MCP1-(His)$_6$ produced in example 2.2 was evaluated by U937 cells. As depicted in FIG. 4, the fusion protein MCP1-(His)$_6$ can enhance cell migration in a dose-dependent manner, in contrast to PBS or $_Q$-MCP1 control, which did not exhibit detectable activity. The functional results suggested that the MCP1 produced by the present expression system exhibited both the N-terminal pGlu structure and the correctly formed disulfide bonds, and thus, functionally enhanced the cell migration.

In conclusion, the working examples demonstrated that the present expression system can be used to precisely and efficiently cyclizing the N-terminal glutaminyl or glutamyl residue of different target proteins to form the pGlu structure. Compared with the conventional method, the target protein produced by the present expression system can be autonomously formed in the host cell, and accordingly, increasing the production efficiency and product yield. Thus, the present expression provided a useful means to efficiently produce different N-terminal pGlu-modified proteins.

It will be understood that the above description of embodiments is given by way of example only and that various modifications may be made by those with ordinary skill in the art. The above specification, examples and data provide a complete description of the structure and use of exemplary embodiments of the invention. Although various embodiments of the invention have been described above with a certain degree of particularity, or with reference to one or more individual embodiments, those with ordinary skill in the art could make numerous alterations to the disclosed embodiments without departing from the spirit or scope of this invention.

What is claimed is:

1. An expression system for producing a target protein having a N-terminal pyroglutamate (pGlu) residue in a host cell, comprising:
 (a) a first vector comprising a first nucleotide sequence encoding a first fusion protein, from the N-terminus to C-terminus, a maltose binding protein (MBP) and a tobacco etch virus protease (TEVP); and
 (b) a second vector comprising in sequence,
  (b-1) a second nucleotide sequence encoding a second fusion protein, from the N-terminus to C-terminus, a thioredoxin (Trx), a S-tag, a linker having a TEVP recognition site (rsTEV) therein, the target protein, and a (His)-6-tag; and
  (b-2) a third nucleotide sequence encoding a glutaminyl cyclase (QC) having a E45Q mutation;
wherein,
 the second nucleotide sequence is characterized in having two restriction endonuclease cleavage sites respectively located within the linker, and between the target protein and the $(His)_6$-tag; and
 the N-terminal pGlu residue of the target protein is autonomously formed in the host cell.

2. The expression system of claim 1, wherein the two restriction endonuclease cleavage sites in the second nucleotide sequence are respectively SnaB I and Xho I.

3. The expression system of claim 1, wherein each of the first, second, and third nucleotide sequences is driven by a promoter selected from the group consisting of T5, T7, tac, trc, lac, lacUV5, araBAD, and rhaBAD.

4. The expression system of claim 3, wherein the promoter is T7 promoter.

5. The expression system of claim 1, wherein the target protein is any of a hormone, a cytokine, a chemokine, an immunoglobulin, or a ribonuclease.

6. The expression system of claim 5, wherein the chemokine is monocyte chemoattractant protein 1 (MCP1) or MCP2.

7. The expression system of claim 5, wherein the hormone is thyrotropin-releasing hormone, gonadotropin-releasing hormone, neurotensin, gastrin, or glucagon.

8. The expression system of claim 5, wherein the cytokine is antineoplastic urinary protein (ANUP) or interferon-γ (IFN-γ).

9. The expression system of claim 5, wherein the immunoglobulin is an antibody with a glutaminyl residue or a glutamyl residue on the N-terminus of light chain or heavy chain.

10. The expression system of claim 5, wherein the ribonuclease is a frog ribonuclease, wherein the frog is selected from the group consisting of *Rana pepeins, Rana japonica,* and *Rana catesbeana.*

11. The expression system of claim 1, wherein the host cell is an *Escherichia coli* (*E. coli*) cell.

12. A method of producing a target protein having a N-terminal pyroglutamate (pGlu) residue in a host cell, comprising:
 (a) transducing the host cell with the expression system of claim 1;
 (b) cultivating the transduced host cell of step (a) in a culture medium;
 (c) lysing the cultivated host cell of step (b); and
 (d) purifying the target protein from the supernatant of the lysed product of step (c) by affinity chromatography.

13. The method of claim 12, wherein the target protein is any of a hormone, a cytokine, a chemokine, an immunoglobulin, or a ribonuclease.

14. The method of claim 13, wherein the chemokine is MCP1 or MCP2.

15. The method of claim 13, wherein the hormone is thyrotropin-releasing hormone, gonadotropin-releasing hormone, neurotensin, gastrin, or glucagon.

16. The method of claim 13, wherein the cytokine is antineoplastic urinary protein (ANUP) or interferon-γ (IFN-γ).

17. The method of claim 13, wherein the immunoglobulin is an antibody with a glutaminyl residue or a glutamyl residue on the N-terminus of light chain or heavy chain.

18. The method of claim 13, wherein the ribonuclease is a frog ribonuclease, wherein the frog is selected from the group consisting of *Rana pepeins, Rana japonica,* and *Rana catesbeana.*

19. The method of claim 12, wherein the host cell is an *E. coli* cell.

20. The method of claim 12, wherein the affinity chromatography is immobilized metal ion affinity chromatography (MIAC).

* * * * *

```
                     SEQUENCE LISTING

<160> NUMBER OF SEQ ID NOS: 31

<210> SEQ ID NO 1
<211> LENGTH: 1977
<212> TYPE: DNA
<213> ORGANISM: Artificial Sequence
<220> FEATURE:
<223> OTHER INFORMATION: MBP-TEVP

<400> SEQUENCE: 1
atgaaaatcg aagaaggtaa actggtaatc tggattaacg gcgataaagg ctataacggt      60
ctcgctgaag tcggtaagaa attcgagaaa gataccggaa ttaaagtcac cgttgagcat     120
ccggataaac tggaagagaa attcccacag gttgcggcaa ctggcgatgg ccctgacatt     180
atcttctggg cacacgaccg ctttggtggc tacgctcaat ctggcctgtt ggctgaaatc     240
accccggaca aagcgttcca ggacaagctg tatccgttta cctgggatgc cgtacgttac     300
aacggcaagc tgattgctta cccgatcgct gttgaagcgt tatcgctgat ttataacaaa     360
gatctgctgc cgaacccgcc aaaaacctgg gaagagatcc cggcgctgga taaagaactg     420
aaagcgaaag gtaagagcgc gctgatgttc aacctgcaag aaccgtactt cacctggccg     480
ctgattgctg ctgacggggg ttatgcgttc aagtatgaaa acggcaagta cgacattaaa     540
gacgtgggcg tggataacgc tggcgcgaaa gcgggtctga ccttcctggt tgacctgatt     600
aaaaacaaac acatgaatgc agacaccgat tactccatcg cagaagctgc ctttaataaa     660
ggcgaaacag cgatgaccat caacggcccg tgggcatggt ccaacatcga caccagcaaa     720
gtgaattatg gtgtaacggt actgccgacc ttcaagggtc aaccatccaa accgttcgtt     780
ggcgtgctga gcgcaggtat taacgccgcc agtccgaaca aagagctggc aaaagagttc     840
ctcgaaaact atctgctgac tgatgaaggt ctggaagcgg ttaataaaga caaaccgctg     900
ggtgccgtag cgctgaagtc ttacgaggaa gagttggcga agatccacg tattgccgcc     960 actatggaaa acgcccagaa aggtgaaatc atgccgaaca tcccgcagat gtccgctttc    1020
tggtatgccg tgcgtactgc ggtgatcaac gccgccagcg gtcgtcagac tgtcgatgaa    1080
gccctgaaag acgcgcagac taattcgagc tcgaacaaca caacaataa caataacaac    1140 aacctcggga tcgagggaag gatttcagaa ttgggagaaa gcttgtttaa gggaccacgt    1200
gattacaacc cgatatcgag caccatttgt catttaacga atgaatctga tgggcacaca    1260
acatcgttgt atggtattgg atttggtccc ttcatcatta caaacaagca cttgtttaga    1320
agaaataatg gaacactgtt ggtccaatca ctacatggtg tattcaaggt caagaacacc    1380
```

```
acgactttgc aacaacacct cattgatggg agggacatga taattattcg catgcctaag    1440
gatttcccac catttcctca aaagctgaaa tttagagagc cacaaaggga agagcgcata    1500
tgtcttgtga caaccaactt ccaaactaag agcatgtcta gcatggtgtc ggacactagt    1560
tgcacattcc cttcatctga tggcatattc tggaagcatt ggattcaaac caaggatggg    1620
cagtgtggca gtccattagt atcaactaga gatgggttca ttgttggtat acactcagca    1680
tcgaatttca ccaacacaaa caattatttc acaagcgtgc cgaaaaactt catgaattg     1740 ttgacaaatc aggaggcgca gcagtggggtt agtggttggc gattaaatgc tgactcagta   1800
ttgtgggggg gccataaagt tttcatggtg aaacctgaag agccttttca gccagttaag   1860
gaagcgactc aactcatgaa tgaattggtg tactcgcaag aaggatttc agaattgggt    1920 accggaggcc tcgaattcgg gctcgagctg ggtgcggcaa ccggcgcagg tggatag      1977
```

<210> SEQ ID NO 2
<211> LENGTH: 1218
<212> TYPE: DNA
<213> ORGANISM: Artificial Sequence
<220> FEATURE:
<223> OTHER INFORMATION: Trx-S-rsTEV-EGFP-6xHis

<400> SEQUENCE: 2

```
atgagcgata aaattattca cctgactgac gacagttttg acacggatgt actcaaagcg     60 gacgggcga tcctcgtcga tttctgggca gagtggtgcg gtccgtgcaa aatgatcgcc    120
ccgattctgg atgaaatcgc tgacgaatat cagggcaaac tgaccgttgc aaaactgaac    180
atcgatcaaa accctggcac tgcgccgaaa tatggcatcc gtggtatccc gactctgctg    240
ctgttcaaaa acggtgaagt ggcggcaacc aaagtgggtg cactgtctaa aggtcagttg    300
aaagagttcc tcgacgctaa cctggccggt tctggttctg gccatatgtc ttctggtggt    360
tctactagta aagaaaccgc tgctgctaaa ttcgaacgcc agcacatgga cagcccagat    420
ctgggtaccg atgacgacga caagatggag aacctgtacg tacagcagtt cgccatggtg    480
agcaagggcg aggagctgtt caccggggtg gtgcccatcc tggtcgagct ggacggcgac    540
gtaaacggcc acaagttcag cgtgtccggc gagggcgagg gcgatgccac ctacggcaag    600
ctgaccctga agttcatctg caccaccggc aagctgcccg tgccctggcc cacccttgtg    660
accaccctga cctacggcgt gcagtgcttc agccgctacc ccgaccacat gaagcagcac    720
gacttcttca gtccgccat gcccgaaggc tacgtccagg agcgcaccat cttcttcaag    780
gacgacggca actacaagac ccgcgccgag gtgaagttcg agggcgacac cctggtgaac    840
cgcatcgagc tgaagggcat cgacttcaag gaggacggca acatcctggg gcacaagctg    900
gagtacaact acaacagcca caacgtctat atcatggccg acaagcagaa gaacggcatc    960
aaggtgaact tcaagatccg ccacaacatc gaggacggca gcgtgcagct cgccgaccac   1020
taccagcaga cacccccat cggcgacggc ccgtgctgc tgcccgacaa ccactacctg     1080
agcacccagt ccgccctgag caaagacccc aacgagaagc gcgatcacat ggtcctgctg   1140
gagttcgtga ccgccgccgg gatcactctc ggcatggacg agctgtacaa gctcgagcac   1200
caccaccacc accactga                                                 1218
```

<210> SEQ ID NO 3
<211> LENGTH: 720
<212> TYPE: DNA
<213> ORGANISM: Artificial Sequence
<220> FEATURE:

<223> OTHER INFORMATION: Trx-S-rsTEV-MCP1-6xHis

<400> SEQUENCE: 3

| | |
|---|---|
| atgagcgata aaattattca cctgactgac gacagttttg acacggatgt actcaaagcg | 60 |
| gacggggcga tcctcgtcga tttctgggca gagtggtgcg gtccgtgcaa aatgatcgcc | 120 |
| ccgattctgg atgaaatcgc tgacgaatat cagggcaaac tgaccgttgc aaaactgaac | 180 |
| atcgatcaaa accctggcac tgcgccgaaa tatggcatcc gtggtatccc gactctgctg | 240 |
| ctgttcaaaa acggtgaagt ggcggcaacc aaagtgggtg cactgtctaa aggtcagttg | 300 |
| aaagagttcc tcgacgctaa cctggccggt tctggttctg ccatatgtc ttctggtggt | 360 |
| tctactagta agaaaccgc tgctgctaaa ttcgaacgcc agcacatgga cagcccagat | 420 |
| ctgggtaccg atgacgacga caagatggag aacctgtacg tacagcagcc agatgcaatc | 480 |
| aatgccccag tcacctgctg ttataacttc accaatagga gatctcagt gcagaggctc | 540 |
| gcgagctata aagaatcac cagcagcaag tgtcccaaag aagctgtgat cttcaagacc | 600 |
| attgtggcca aggagatctg tgctgacccc aagcagaagt gggttcagga ttccatggac | 660 |
| cacctggaca agcaaaccca aactccgaag actctcgagc accaccaca ccaccactga | 720 |

<210> SEQ ID NO 4
<211> LENGTH: 801
<212> TYPE: DNA
<213> ORGANISM: Artificial Sequence
<220> FEATURE:
<223> OTHER INFORMATION: QC (E45Q)

<400> SEQUENCE: 4

| | |
|---|---|
| atgccacgtc tcgtccctgc cctgctactc atcctcgcac tcctgccggc catggcagtt | 60 |
| gcccgcgacc cggtcccgac gcagggctat cgcgtggtca agcgctatcc gcacgacacc | 120 |
| actgcccttta cccaaggcct gttttatctg cgcggccatc tgtacgaaag cactggcgag | 180 |
| accgggcgtt cgagcgtgcg caaggtggac ctggaaacag gcgcatcct gcaacgcgcc | 240 |
| gaggtgccgc caccgtattt cggcgaaggc atcgtggcct ggcgcgaccg cctgatccag | 300 |
| ctgacctggc gtaaccacga aggcttcgtc tacgacctgg cgacgctgac gccacgcgcg | 360 |
| cgtttccgct atccgggcga aggctggcg ctgaccagcg atgacagcca cctgtacatg | 420 |
| agcgacggca ccgccgtgat ccgcaaactg gatccggaca cattgcagca ggtcggcagc | 480 |
| atcaaggtca ccgccggcgg ccggccgctg gacaatctca acgagctgga atgggtcaac | 540 |
| ggcgagctgc tagccaatgt ctggctgacc tcgcgcattg cgcgcatcga tccagccagc | 600 |
| ggcaaggtag tggcctggat cgacctgcaa gcgctcgtgc cggacgccga cgcactgacc | 660 |
| gactccacca cgatgtgct caacggcatc gcattgacg ccgagcacga ccgcttgttc | 720 |
| gtcaccggca acgttggcc gatgctctat gaaatccggc tcacaccact gccgcacgcc | 780 |
| gcggccggca agcacgcgca g | 801 |

<210> SEQ ID NO 5
<211> LENGTH: 658
<212> TYPE: PRT
<213> ORGANISM: Artificial Sequence
<220> FEATURE:
<223> OTHER INFORMATION: MBP-TEVP

<400> SEQUENCE: 5

Met Lys Ile Glu Glu Gly Lys Leu Val Ile Trp Ile Asn Gly Asp Lys
1               5                   10                  15

-continued

```
Gly Tyr Asn Gly Leu Ala Glu Val Gly Lys Lys Phe Glu Lys Asp Thr
             20                  25                  30

Gly Ile Lys Val Thr Val Glu His Pro Asp Lys Leu Glu Glu Lys Phe
         35                  40                  45

Pro Gln Val Ala Ala Thr Gly Asp Gly Pro Asp Ile Ile Phe Trp Ala
 50                  55                  60

His Asp Arg Phe Gly Gly Tyr Ala Gln Ser Gly Leu Leu Ala Glu Ile
 65                  70                  75                  80

Thr Pro Asp Lys Ala Phe Gln Asp Lys Leu Tyr Pro Phe Thr Trp Asp
                 85                  90                  95

Ala Val Arg Tyr Asn Gly Lys Leu Ile Ala Tyr Pro Ile Ala Val Glu
            100                 105                 110

Ala Leu Ser Leu Ile Tyr Asn Lys Asp Leu Leu Pro Asn Pro Pro Lys
        115                 120                 125

Thr Trp Glu Glu Ile Pro Ala Leu Asp Lys Glu Leu Lys Ala Lys Gly
    130                 135                 140

Lys Ser Ala Leu Met Phe Asn Leu Gln Glu Pro Tyr Phe Thr Trp Pro
145                 150                 155                 160

Leu Ile Ala Ala Asp Gly Gly Tyr Ala Phe Lys Tyr Glu Asn Gly Lys
                165                 170                 175

Tyr Asp Ile Lys Asp Val Gly Val Asp Asn Ala Gly Ala Lys Ala Gly
            180                 185                 190

Leu Thr Phe Leu Val Asp Leu Ile Lys Asn Lys His Met Asn Ala Asp
        195                 200                 205

Thr Asp Tyr Ser Ile Ala Glu Ala Ala Phe Asn Lys Gly Glu Thr Ala
    210                 215                 220

Met Thr Ile Asn Gly Pro Trp Ala Trp Ser Asn Ile Asp Thr Ser Lys
225                 230                 235                 240

Val Asn Tyr Gly Val Thr Val Leu Pro Thr Phe Lys Gly Gln Pro Ser
                245                 250                 255

Lys Pro Phe Val Gly Val Leu Ser Ala Gly Ile Asn Ala Ala Ser Pro
            260                 265                 270

Asn Lys Glu Leu Ala Lys Glu Phe Leu Glu Asn Tyr Leu Leu Thr Asp
        275                 280                 285

Glu Gly Leu Glu Ala Val Asn Lys Asp Lys Pro Leu Gly Ala Val Ala
    290                 295                 300

Leu Lys Ser Tyr Glu Glu Glu Leu Ala Lys Asp Pro Arg Ile Ala Ala
305                 310                 315                 320

Thr Met Glu Asn Ala Gln Lys Gly Glu Ile Met Pro Asn Ile Pro Gln
                325                 330                 335

Met Ser Ala Phe Trp Tyr Ala Val Arg Thr Ala Val Ile Asn Ala Ala
            340                 345                 350

Ser Gly Arg Gln Thr Val Asp Glu Ala Leu Lys Asp Ala Gln Thr Asn
        355                 360                 365

Ser Ser Ser Asn Asn Asn Asn Asn Asn Asn Asn Leu Gly Ile
    370                 375                 380

Glu Gly Arg Ile Ser Glu Leu Gly Glu Ser Leu Phe Lys Gly Pro Arg
385                 390                 395                 400

Asp Tyr Asn Pro Ile Ser Ser Thr Ile Cys His Leu Thr Asn Glu Ser
                405                 410                 415

Asp Gly His Thr Thr Ser Leu Tyr Gly Ile Gly Phe Gly Pro Phe Ile
            420                 425                 430

Ile Thr Asn Lys His Leu Phe Arg Arg Asn Asn Gly Thr Leu Leu Val
```

```
            435                 440                 445
Gln Ser Leu His Gly Val Phe Lys Val Lys Asn Thr Thr Leu Gln
    450                 455                 460

Gln His Leu Ile Asp Gly Arg Asp Met Ile Ile Arg Met Pro Lys
465                 470                 475                 480

Asp Phe Pro Pro Phe Pro Gln Lys Leu Lys Phe Arg Glu Pro Gln Arg
                485                 490                 495

Glu Glu Arg Ile Cys Leu Val Thr Thr Asn Phe Gln Thr Lys Ser Met
                500                 505                 510

Ser Ser Met Val Ser Asp Thr Ser Cys Thr Phe Pro Ser Ser Asp Gly
        515                 520                 525

Ile Phe Trp Lys His Trp Ile Gln Thr Lys Asp Gly Gln Cys Gly Ser
    530                 535                 540

Pro Leu Val Ser Thr Arg Asp Gly Phe Ile Val Gly Ile His Ser Ala
545                 550                 555                 560

Ser Asn Phe Thr Asn Thr Asn Asn Tyr Phe Thr Ser Val Pro Lys Asn
                565                 570                 575

Phe Met Glu Leu Leu Thr Asn Gln Glu Ala Gln Gln Trp Val Ser Gly
                580                 585                 590

Trp Arg Leu Asn Ala Asp Ser Val Leu Trp Gly Gly His Lys Val Phe
            595                 600                 605

Met Val Lys Pro Glu Glu Pro Phe Gln Pro Val Lys Glu Ala Thr Gln
        610                 615                 620

Leu Met Asn Glu Leu Val Tyr Ser Gln Gly Arg Ile Ser Glu Leu Gly
625                 630                 635                 640

Thr Gly Gly Leu Glu Phe Gly Leu Glu Leu Gly Ala Ala Thr Gly Ala
                645                 650                 655

Gly Gly

<210> SEQ ID NO 6
<211> LENGTH: 405
<212> TYPE: PRT
<213> ORGANISM: Artificial Sequence
<220> FEATURE:
<223> OTHER INFORMATION: Trx-S-rsTEV-EGFP-6xHis

<400> SEQUENCE: 6

Met Ser Asp Lys Ile Ile His Leu Thr Asp Asp Ser Phe Asp Thr Asp
1               5                   10                  15

Val Leu Lys Ala Asp Gly Ala Ile Leu Val Asp Phe Trp Ala Glu Trp
                20                  25                  30

Cys Gly Pro Cys Lys Met Ile Ala Pro Ile Leu Asp Glu Ile Ala Asp
            35                  40                  45

Glu Tyr Gln Gly Lys Leu Thr Val Ala Lys Leu Asn Ile Asp Gln Asn
        50                  55                  60

Pro Gly Thr Ala Pro Lys Tyr Gly Ile Arg Gly Ile Pro Thr Leu Leu
65                  70                  75                  80

Leu Phe Lys Asn Gly Glu Val Ala Ala Thr Lys Val Gly Ala Leu Ser
                85                  90                  95

Lys Gly Gln Leu Lys Glu Phe Leu Asp Ala Asn Leu Ala Gly Ser Gly
            100                 105                 110

Ser Gly His Met Ser Ser Gly Gly Ser Thr Lys Glu Thr Ala Ala
        115                 120                 125

Ala Lys Phe Glu Arg Gln His Met Asp Ser Pro Asp Leu Gly Thr Asp
    130                 135                 140
```

```
Asp Asp Asp Lys Met Glu Asn Leu Tyr Val Gln Gln Phe Ala Met Val
145                 150                 155                 160

Ser Lys Gly Glu Glu Leu Phe Thr Gly Val Val Pro Ile Leu Val Glu
            165                 170                 175

Leu Asp Gly Asp Val Asn Gly His Lys Phe Ser Val Ser Gly Glu Gly
            180                 185                 190

Glu Gly Asp Ala Thr Tyr Gly Lys Leu Thr Leu Lys Phe Ile Cys Thr
            195                 200                 205

Thr Gly Lys Leu Pro Val Pro Trp Pro Thr Leu Val Thr Thr Leu Thr
            210                 215                 220

Tyr Gly Val Gln Cys Phe Ser Arg Tyr Pro Asp His Met Lys Gln His
225                 230                 235                 240

Asp Phe Phe Lys Ser Ala Met Pro Glu Gly Tyr Val Gln Glu Arg Thr
            245                 250                 255

Ile Phe Phe Lys Asp Asp Gly Asn Tyr Lys Thr Arg Ala Glu Val Lys
            260                 265                 270

Phe Glu Gly Asp Thr Leu Val Asn Arg Ile Glu Leu Lys Gly Ile Asp
            275                 280                 285

Phe Lys Glu Asp Gly Asn Ile Leu Gly His Lys Leu Glu Tyr Asn Tyr
            290                 295                 300

Asn Ser His Asn Val Tyr Ile Met Ala Asp Lys Gln Lys Asn Gly Ile
305                 310                 315                 320

Lys Val Asn Phe Lys Ile Arg His Asn Ile Glu Asp Gly Ser Val Gln
            325                 330                 335

Leu Ala Asp His Tyr Gln Gln Asn Thr Pro Ile Gly Asp Gly Pro Val
            340                 345                 350

Leu Leu Pro Asp Asn His Tyr Leu Ser Thr Gln Ser Ala Leu Ser Lys
            355                 360                 365

Asp Pro Asn Glu Lys Arg Asp His Met Val Leu Leu Glu Phe Val Thr
            370                 375                 380

Ala Ala Gly Ile Thr Leu Gly Met Asp Glu Leu Tyr Lys Leu Glu His
385                 390                 395                 400

His His His His
            405

<210> SEQ ID NO 7
<211> LENGTH: 239
<212> TYPE: PRT
<213> ORGANISM: Artificial Sequence
<220> FEATURE:
<223> OTHER INFORMATION: Trx-S-rsTEV-MCP1-6xHis

<400> SEQUENCE: 7

Met Ser Asp Lys Ile Ile His Leu Thr Asp Asp Ser Phe Asp Thr Asp
1               5                   10                  15

Val Leu Lys Ala Asp Gly Ala Ile Leu Val Asp Phe Trp Ala Glu Trp
            20                  25                  30

Cys Gly Pro Cys Lys Met Ile Ala Pro Ile Leu Asp Glu Ile Ala Asp
            35                  40                  45

Glu Tyr Gln Gly Lys Leu Thr Val Ala Lys Leu Asn Ile Asp Gln Asn
            50                  55                  60

Pro Gly Thr Ala Pro Lys Tyr Gly Ile Arg Gly Ile Pro Thr Leu Leu
65                  70                  75                  80

Leu Phe Lys Asn Gly Glu Val Ala Ala Thr Lys Val Gly Ala Leu Ser
            85                  90                  95
```

Lys Gly Gln Leu Lys Glu Phe Leu Asp Ala Asn Leu Ala Gly Ser Gly
            100                 105                 110

Ser Gly His Met Ser Ser Gly Ser Thr Ser Lys Glu Thr Ala Ala
            115                 120                 125

Ala Lys Phe Glu Arg Gln His Met Asp Ser Pro Asp Leu Gly Thr Asp
        130                 135                 140

Asp Asp Asp Lys Met Glu Asn Leu Tyr Val Gln Gln Pro Asp Ala Ile
145                 150                 155                 160

Asn Ala Pro Val Thr Cys Cys Tyr Asn Phe Thr Asn Arg Lys Ile Ser
                165                 170                 175

Val Gln Arg Leu Ala Ser Tyr Arg Arg Ile Thr Ser Ser Lys Cys Pro
            180                 185                 190

Lys Glu Ala Val Ile Phe Lys Thr Ile Val Ala Lys Glu Ile Cys Ala
            195                 200                 205

Asp Pro Lys Gln Lys Trp Val Gln Asp Ser Met Asp His Leu Asp Lys
        210                 215                 220

Gln Thr Gln Thr Pro Lys Thr Leu Glu His His His His His
225                 230                 235

<210> SEQ ID NO 8
<211> LENGTH: 267
<212> TYPE: PRT
<213> ORGANISM: Artificial Sequence
<220> FEATURE:
<223> OTHER INFORMATION: QC (E45Q)

<400> SEQUENCE: 8

Met Pro Arg Leu Val Pro Ala Leu Leu Leu Ile Leu Ala Leu Leu Pro
1               5                   10                  15

Ala Met Ala Val Ala Arg Asp Pro Val Pro Thr Gln Gly Tyr Arg Val
            20                  25                  30

Val Lys Arg Tyr Pro His Asp Thr Thr Ala Phe Thr Gln Gly Leu Phe
        35                  40                  45

Tyr Leu Arg Gly His Leu Tyr Glu Ser Thr Gly Glu Thr Gly Arg Ser
    50                  55                  60

Ser Val Arg Lys Val Asp Leu Glu Thr Gly Arg Ile Leu Gln Arg Ala
65                  70                  75                  80

Glu Val Pro Pro Tyr Phe Gly Glu Gly Ile Val Ala Trp Arg Asp
                85                  90                  95

Arg Leu Ile Gln Leu Thr Trp Arg Asn His Glu Gly Phe Val Tyr Asp
            100                 105                 110

Leu Ala Thr Leu Thr Pro Arg Ala Arg Phe Arg Tyr Pro Gly Glu Gly
        115                 120                 125

Trp Ala Leu Thr Ser Asp Asp Ser His Leu Tyr Met Ser Asp Gly Thr
    130                 135                 140

Ala Val Ile Arg Lys Leu Asp Pro Asp Thr Leu Gln Gln Val Gly Ser
145                 150                 155                 160

Ile Lys Val Thr Ala Gly Gly Arg Pro Leu Asp Asn Leu Asn Glu Leu
                165                 170                 175

Glu Trp Val Asn Gly Glu Leu Leu Ala Asn Val Trp Leu Thr Ser Arg
            180                 185                 190

Ile Ala Arg Ile Asp Pro Ala Ser Gly Lys Val Val Ala Trp Ile Asp
        195                 200                 205

Leu Gln Ala Leu Val Pro Asp Ala Asp Ala Leu Thr Asp Ser Thr Asn
    210                 215                 220

-continued

```
Asp Val Leu Asn Gly Ile Ala Phe Asp Ala Glu His Asp Arg Leu Phe
225                 230                 235                 240

Val Thr Gly Lys Arg Trp Pro Met Leu Tyr Glu Ile Arg Leu Thr Pro
            245                 250                 255

Leu Pro His Ala Ala Ala Gly Lys His Ala Gln
        260                 265

<210> SEQ ID NO 9
<211> LENGTH: 21
<212> TYPE: DNA
<213> ORGANISM: Artificial Sequence
<220> FEATURE:
<223> OTHER INFORMATION: Forward Primer for MBP-TEVP-1

<400> SEQUENCE: 9
aaaatcgaag aaggtaaact g                                           21

<210> SEQ ID NO 10
<211> LENGTH: 25
<212> TYPE: DNA
<213> ORGANISM: Artificial Sequence
<220> FEATURE:
<223> OTHER INFORMATION: Forward Primer for MBP-TEVP-2

<400> SEQUENCE: 10
catgaaaatc gaagaaggta aactg                                       25

<210> SEQ ID NO 11
<211> LENGTH: 21
<212> TYPE: DNA
<213> ORGANISM: Artificial Sequence
<220> FEATURE:
<223> OTHER INFORMATION: Reverse Primer for MBP-TEVP-1

<400> SEQUENCE: 11
ctatccacct gcgccggttg c                                           21

<210> SEQ ID NO 12
<211> LENGTH: 25
<212> TYPE: DNA
<213> ORGANISM: Artificial Sequence
<220> FEATURE:
<223> OTHER INFORMATION: Reverse Primer for MBP-TEVP-2

<400> SEQUENCE: 12
tcgactatcc acctgcgccg gttgc                                       25

<210> SEQ ID NO 13
<211> LENGTH: 33
<212> TYPE: DNA
<213> ORGANISM: Artificial Sequence
<220> FEATURE:
<223> OTHER INFORMATION: Forward primer-EGFP

<400> SEQUENCE: 13
gacgacgaca agatggagaa cctgtacgta cag                              33

<210> SEQ ID NO 14
<211> LENGTH: 33
<212> TYPE: DNA
<213> ORGANISM: Artificial Sequence
<220> FEATURE:
<223> OTHER INFORMATION: Reverse primer-EGFP

<400> SEQUENCE: 14
```
cgcgggcggc cgttctcagt ggtggtggtg gtg                                    33

<210> SEQ ID NO 15
<211> LENGTH: 33
<212> TYPE: DNA
<213> ORGANISM: Artificial Sequence
<220> FEATURE:
<223> OTHER INFORMATION: Forward primer-QC (E45Q)

<400> SEQUENCE: 15
gcgggcccgg ccttgatgcc acgtctcgtc cct                                    33

<210> SEQ ID NO 16
<211> LENGTH: 36
<212> TYPE: DNA
<213> ORGANISM: Artificial Sequence
<220> FEATURE:
<223> OTHER INFORMATION: Reverse primer-QC (E45Q)

<400> SEQUENCE: 16
gaggagaagc ccggtttact gcgcgtgctt gccggc                                 36

<210> SEQ ID NO 17
<211> LENGTH: 39
<212> TYPE: DNA
<213> ORGANISM: Artificial Sequence
<220> FEATURE:
<223> OTHER INFORMATION: Site-directed mutagenesis-QFA insertion-1

<400> SEQUENCE: 17
gagaacctgt acgtacagca gttcgccatg gtgagcaag                              39

<210> SEQ ID NO 18
<211> LENGTH: 39
<212> TYPE: DNA
<213> ORGANISM: Artificial Sequence
<220> FEATURE:
<223> OTHER INFORMATION: Site-directed mutagenesis-QFA insertion-2

<400> SEQUENCE: 18
cttgctcacc atggcgaact gctgtacgta caggttctc                              39

<210> SEQ ID NO 19
<211> LENGTH: 39
<212> TYPE: DNA
<213> ORGANISM: Artificial Sequence
<220> FEATURE:
<223> OTHER INFORMATION: Site-directed mutagenesis-QPG insertion-1

<400> SEQUENCE: 19
gagaacctgt acgtacagca gccaggcatg gtgagcaag                              39

<210> SEQ ID NO 20
<211> LENGTH: 39
<212> TYPE: DNA
<213> ORGANISM: Artificial Sequence
<220> FEATURE:
<223> OTHER INFORMATION: Site-directed mutagenesis-QPG insertion-2

<400> SEQUENCE: 20
cttgctcacc atgcctggct gctgtacgta caggttctc                              39

<210> SEQ ID NO 21
<211> LENGTH: 1218
<212> TYPE: DNA

<213> ORGANISM: Artificial Sequence
<220> FEATURE:
<223> OTHER INFORMATION: Trx-S-rsTEV-QPGEGFP-6xHis

<400> SEQUENCE: 21

```
atgagcgata aaattattca cctgactgac gacagttttg acacggatgt actcaaagcg      60
gacgggcga tcctcgtcga tttctgggca gagtggtgcg gtccgtgcaa aatgatcgcc     120
ccgattctgg atgaaatcgc tgacgaatat cagggcaaac tgaccgttgc aaaactgaac     180
atcgatcaaa accctggcac tgcgccgaaa tatggcatcc gtggtatccc gactctgctg     240
ctgttcaaaa acggtgaagt ggcggcaacc aaagtgggtg cactgtctaa aggtcagttg     300
aaagagttcc tcgacgctaa cctggccggt tctggttctg gccatatgtc ttctggtggt     360
tctactagta agaaaccgc tgctgctaaa ttcgaacgcc agcacatgga cagcccagat     420
ctgggtaccg atgacgacga caagatggag aacctgtacg tacagcagcc aggcatggtg     480
agcaagggcg aggagctgtt caccggggtg gtgcccatcc tggtcgagct ggacggcgac     540
gtaaacggcc acaagttcag cgtgtccggc gagggcgagg gcgatgccac ctacggcaag     600
ctgacccctg agttcatctg caccaccggc aagctgcccg tgccctggcc caccctcgtg     660
accaccctga cctacggcgt gcagtgcttc agccgctacc cgaccacat gaagcagcac     720
gacttcttca gtccgccat gcccgaaggc tacgtccagg agcgcaccat cttcttcaag     780
gacgacggca actacaagac ccgcgccgag gtgaagttcg agggcgacac cctggtgaac     840
cgcatcgagc tgaagggcat cgacttcaag gaggacggca acatcctggg cacaagctg     900
gagtacaact acaacagcca caacgtctat atcatggccg acaagcagaa gaacggcatc     960
aaggtgaact tcaagatccg ccacaacatc gaggacggca gcgtgcagct cgccgaccac    1020
taccagcaga cacccccat cggcgacggc cccgtgctgc tgcccgacaa ccactacctg    1080
agcacccagt ccgccctgag caaagacccc aacgagaagc gcgatcacat ggtcctgctg    1140
gagttcgtga ccgccgccgg gatcactctc ggcatggacg agctgtacaa gctcgagcac    1200
caccaccacc accactga                                                  1218
```

<210> SEQ ID NO 22
<211> LENGTH: 405
<212> TYPE: PRT
<213> ORGANISM: Artificial Sequence
<220> FEATURE:
<223> OTHER INFORMATION: Trx-S-rsTEV-QPGEGFP-6xHis

<400> SEQUENCE: 22

```
Met Ser Asp Lys Ile Ile His Leu Thr Asp Asp Ser Phe Asp Thr Asp
1               5                   10                  15

Val Leu Lys Ala Asp Gly Ala Ile Leu Val Asp Phe Trp Ala Glu Trp
            20                  25                  30

Cys Gly Pro Cys Lys Met Ile Ala Pro Ile Leu Asp Glu Ile Ala Asp
        35                  40                  45

Glu Tyr Gln Gly Lys Leu Thr Val Ala Lys Leu Asn Ile Asp Gln Asn
    50                  55                  60

Pro Gly Thr Ala Pro Lys Tyr Gly Ile Arg Gly Ile Pro Thr Leu Leu
65                  70                  75                  80

Leu Phe Lys Asn Gly Glu Val Ala Ala Thr Lys Val Gly Ala Leu Ser
                85                  90                  95

Lys Gly Gln Leu Lys Glu Phe Leu Asp Ala Asn Leu Ala Gly Ser Gly
            100                 105                 110
```

```
Ser Gly His Met Ser Ser Gly Ser Thr Ser Lys Glu Thr Ala Ala
            115                 120                 125
Ala Lys Phe Glu Arg Gln His Met Asp Ser Pro Asp Leu Gly Thr Asp
130                 135                 140
Asp Asp Asp Lys Met Glu Asn Leu Tyr Val Gln Gln Pro Gly Met Val
145                 150                 155                 160
Ser Lys Gly Glu Glu Leu Phe Thr Gly Val Val Pro Ile Leu Val Glu
                165                 170                 175
Leu Asp Gly Asp Val Asn Gly His Lys Phe Ser Val Ser Gly Glu Gly
            180                 185                 190
Glu Gly Asp Ala Thr Tyr Gly Lys Leu Thr Leu Lys Phe Ile Cys Thr
        195                 200                 205
Thr Gly Lys Leu Pro Val Pro Trp Pro Thr Leu Val Thr Thr Leu Thr
210                 215                 220
Tyr Gly Val Gln Cys Phe Ser Arg Tyr Pro Asp His Met Lys Gln His
225                 230                 235                 240
Asp Phe Phe Lys Ser Ala Met Pro Glu Gly Tyr Val Gln Glu Arg Thr
                245                 250                 255
Ile Phe Phe Lys Asp Asp Gly Asn Tyr Lys Thr Arg Ala Glu Val Lys
            260                 265                 270
Phe Glu Gly Asp Thr Leu Val Asn Arg Ile Glu Leu Lys Gly Ile Asp
        275                 280                 285
Phe Lys Glu Asp Gly Asn Ile Leu Gly His Lys Leu Glu Tyr Asn Tyr
290                 295                 300
Asn Ser His Asn Val Tyr Ile Met Ala Asp Lys Gln Lys Asn Gly Ile
305                 310                 315                 320
Lys Val Asn Phe Lys Ile Arg His Asn Ile Glu Asp Gly Ser Val Gln
                325                 330                 335
Leu Ala Asp His Tyr Gln Gln Asn Thr Pro Ile Gly Asp Gly Pro Val
            340                 345                 350
Leu Leu Pro Asp Asn His Tyr Leu Ser Thr Gln Ser Ala Leu Ser Lys
        355                 360                 365
Asp Pro Asn Glu Lys Arg Asp His Met Val Leu Leu Glu Phe Val Thr
370                 375                 380
Ala Ala Gly Ile Thr Leu Gly Met Asp Glu Leu Tyr Lys Leu Glu His
385                 390                 395                 400
His His His His
            405

<210> SEQ ID NO 23
<211> LENGTH: 21
<212> TYPE: DNA
<213> ORGANISM: Artificial Sequence
<220> FEATURE:
<223> OTHER INFORMATION: Forward primer-MCP1

<400> SEQUENCE: 23
gtacagcagc cagatgcaat c                                            21

<210> SEQ ID NO 24
<211> LENGTH: 23
<212> TYPE: DNA
<213> ORGANISM: Artificial Sequence
<220> FEATURE:
<223> OTHER INFORMATION: Reverse primer-MCP1-1

<400> SEQUENCE: 24
```
tcgagagtct tcggagtttg ggt                                              23

<210> SEQ ID NO 25
<211> LENGTH: 19
<212> TYPE: DNA
<213> ORGANISM: Artificial Sequence
<220> FEATURE:
<223> OTHER INFORMATION: Reverse primer-MCP1-2

<400> SEQUENCE: 25
gagtcttcgg agtttgggt                                                   19

<210> SEQ ID NO 26
<211> LENGTH: 801
<212> TYPE: DNA
<213> ORGANISM: Artificial Sequence
<220> FEATURE:
<223> OTHER INFORMATION: QC (E89A)

<400> SEQUENCE: 26
atgccacgtc tcgtccctgc cctgctactc atcctcgcac tcctgccggc catggcagtt        60
gcccgcgacc cggtcccgac gcagggctat cgcgtggtca agcgctatcc gcacgacacc       120
actgccttta ccgaaggcct gttttatctg cgcggccatc tgtacgaaag cactggcgag       180 accggcgtt cgagcgtgcg caaggtggac ctggaaacag gcgcatcct gcaacgcgcc        240 gaggtgccgc caccgtattt cggcgcaggc atcgtggcct ggcgcgaccg cctgatccag       300
ctgacctggc gtaaccacga aggcttcgtc tacgacctgg cgacgctgac gccacgcgcg       360
cgtttccgct atccgggcga aggctgggcg ctgaccagcg atgacagcca cctgtacatg       420
agcgacggca ccgccgtgat ccgcaaactg gatccggaca cattgcagca ggtcggcagc       480
atcaaggtca ccgccggcgg ccggccgctg acaatctca acgagctgga atgggtcaac       540
ggcgagctgc tagccaatgt ctggctgacc tcgcgcattg cgcgcatcga tccagccagc       600
ggcaaggtag tggcctggat cgacctgcaa gcgctcgtgc cggacgccga cgcactgacc       660
gactccacca acgatgtgct caacggcatc gcattcgacg ccgagcacga ccgcttgttc       720
gtcaccggca aacgttggcc gatgctctat gaaatccggc tcacaccact gccgcacgcc       780
gcggccggca agcacgcgca g                                                801

<210> SEQ ID NO 27
<211> LENGTH: 267
<212> TYPE: PRT
<213> ORGANISM: Artificial Sequence
<220> FEATURE:
<223> OTHER INFORMATION: QC (E89A)

<400> SEQUENCE: 27

Met Pro Arg Leu Val Pro Ala Leu Leu Leu Ile Leu Ala Leu Leu Pro
1               5                   10                  15

Ala Met Ala Val Ala Arg Asp Pro Val Pro Thr Gln Gly Tyr Arg Val
            20                  25                  30

Val Lys Arg Tyr Pro His Asp Thr Thr Ala Phe Thr Glu Gly Leu Phe
        35                  40                  45

Tyr Leu Arg Gly His Leu Tyr Glu Ser Thr Gly Glu Thr Gly Arg Ser
    50                  55                  60

Ser Val Arg Lys Val Asp Leu Glu Thr Gly Arg Ile Leu Gln Arg Ala
65                  70                  75                  80

Glu Val Pro Pro Pro Tyr Phe Gly Ala Gly Ile Val Ala Trp Arg Asp
                85                  90                  95

```
Arg Leu Ile Gln Leu Thr Trp Arg Asn His Glu Gly Phe Val Tyr Asp
            100                 105                 110
Leu Ala Thr Leu Thr Pro Arg Ala Arg Phe Arg Tyr Pro Gly Glu Gly
        115                 120                 125
Trp Ala Leu Thr Ser Asp Asp Ser His Leu Tyr Met Ser Asp Gly Thr
130                 135                 140
Ala Val Ile Arg Lys Leu Asp Pro Asp Thr Leu Gln Gln Val Gly Ser
145                 150                 155                 160
Ile Lys Val Thr Ala Gly Gly Arg Pro Leu Asp Asn Leu Asn Glu Leu
                165                 170                 175
Glu Trp Val Asn Gly Leu Leu Ala Asn Val Trp Leu Thr Ser Arg
            180                 185                 190
Ile Ala Arg Ile Asp Pro Ala Ser Gly Lys Val Val Ala Trp Ile Asp
        195                 200                 205
Leu Gln Ala Leu Val Pro Asp Ala Asp Ala Leu Thr Asp Ser Thr Asn
210                 215                 220
Asp Val Leu Asn Gly Ile Ala Phe Asp Ala Glu His Asp Arg Leu Phe
225                 230                 235                 240
Val Thr Gly Lys Arg Trp Pro Met Leu Tyr Glu Ile Arg Leu Thr Pro
                245                 250                 255
Leu Pro His Ala Ala Ala Gly Lys His Ala Gln
            260                 265

<210> SEQ ID NO 28
<211> LENGTH: 228
<212> TYPE: DNA
<213> ORGANISM: Artificial Sequence
<220> FEATURE:
<223> OTHER INFORMATION: MCP1

<400> SEQUENCE: 28
cagccagatg caatcaatgc cccagtcacc tgctgttata acttcaccaa taggaagatc    60
tcagtgcaga ggctcgcgag ctatagaaga atcaccagca gcaagtgtcc caaagaagct   120
gtgatcttca agaccattgt ggccaaggag atctgtgctg accccaagca gaagtgggtt   180
caggattcca tggaccacct ggacaagcaa acccaaactc gaagact                 228

<210> SEQ ID NO 29
<211> LENGTH: 9
<212> TYPE: PRT
<213> ORGANISM: Artificial Sequence
<220> FEATURE:
<223> OTHER INFORMATION: rsTEV sequence-1

<400> SEQUENCE: 29

Glu Asn Leu Tyr Val Gln Gln Phe Ala
1               5

<210> SEQ ID NO 30
<211> LENGTH: 9
<212> TYPE: PRT
<213> ORGANISM: Artificial Sequence
<220> FEATURE:
<223> OTHER INFORMATION: rsTEV sequence-2

<400> SEQUENCE: 30

Glu Asn Leu Tyr Val Gln Gln Pro Gly
1               5
```

```
<210> SEQ ID NO 31
<211> LENGTH: 7
<212> TYPE: PRT
<213> ORGANISM: Artificial Sequence
<220> FEATURE:
<223> OTHER INFORMATION: rsTEV sequence-3

<400> SEQUENCE: 31

Glu Asn Leu Tyr Val Gln Gln
1               5
```